United States Patent [19]

Jezl et al.

[11] Patent Number: 5,080,872
[45] Date of Patent: Jan. 14, 1992

[54] TEMPERATURE REGULATING REACTOR APPARATUS AND METHOD

[75] Inventors: James L. Jezl, St. Charles; Robert F. Blanks, Geneva; Michael A. Stasi, Downers Grove, all of Ill.

[73] Assignee: Amoco Corporation, Chicago, Ill.

[21] Appl. No.: 295,226

[22] Filed: Jan. 9, 1989

Related U.S. Application Data

[60] Continuation-in-part of Ser. No. 237,141, Aug. 26, 1988, abandoned, which is a division of Ser. No. 19,413, Feb. 26, 1987, Pat. No. 4,778,826, which is a division of Ser. No. 781,214, Sep. 26, 1985, Pat. No. 4,654,458.

[51] Int. Cl.$^5$ ............................................. B01J 8/02
[52] U.S. Cl. ...................... 422/201; 422/148; 422/211
[58] Field of Search ................ 422/148, 197, 201, 211

[56] References Cited

U.S. PATENT DOCUMENTS

| | | | |
|---|---|---|---|
| 2,066,198 | 12/1936 | Buc | 422/201 |
| 2,306,011 | 12/1942 | Burk et al. | |
| 2,410,670 | 11/1946 | Manderstam | 422/197 |

Primary Examiner—Jill Johnston
Attorney, Agent, or Firm—Nick C. Kottis; William H. Magidson; Ralph C. Medhurst

[57] ABSTRACT

A reactor apparatus and method useful in regulating temperature in a heterogeneous reaction system is provided. The apparatus includes an elongated tube reactor packed with a bed of solid particles through which a reactant fluid phase is passed. A plurality of heat transfer medium passage tubes are disposed in the bed of solid particles with adjacent tubes spaced relative to each other about the longitudinal axis of the reactor and with the tubes being substantially transverse to reactant flow through the reactor. The temperature in the system may, in turn, be regulated by effecting flow of a heat transfer medium through the passage tubes.

36 Claims, 5 Drawing Sheets

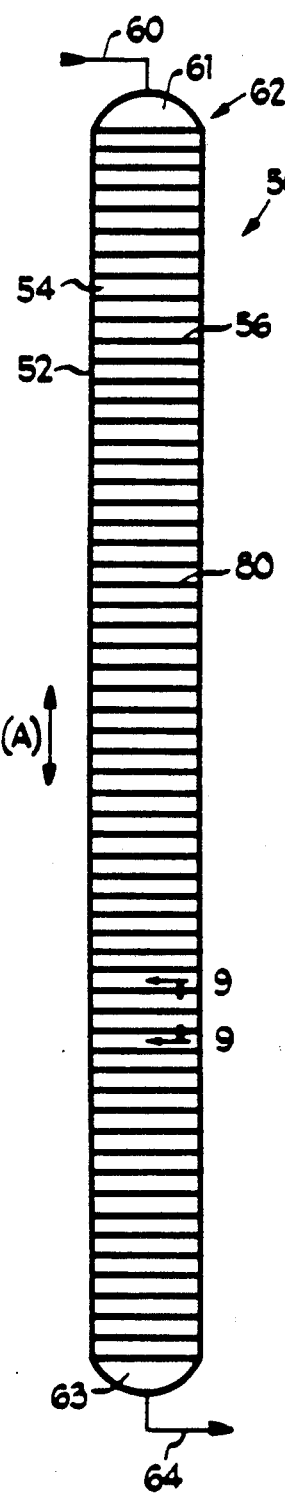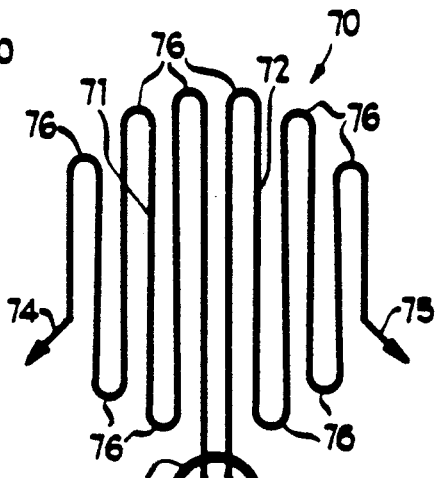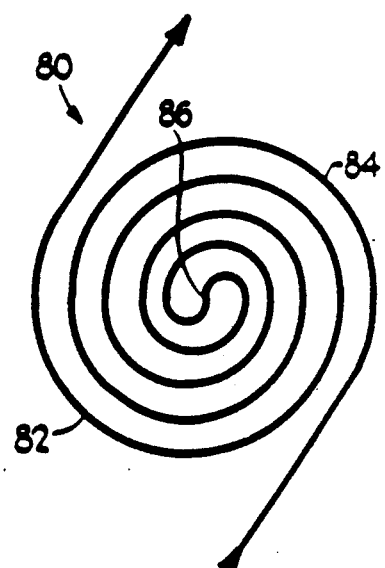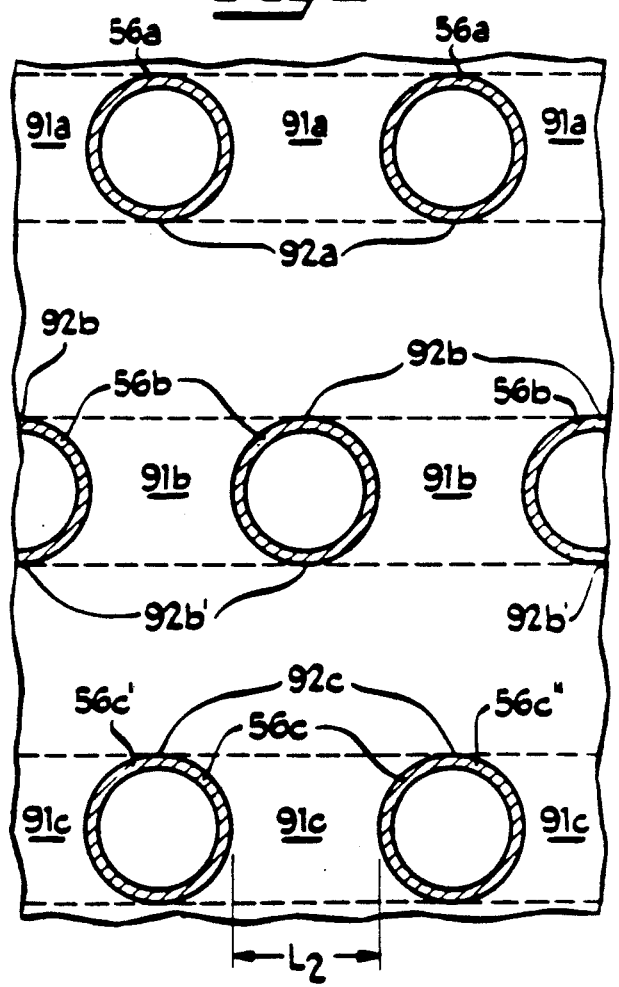

TEMPERATURE REGULATING REACTOR APPARATUS AND METHOD

CROSS REFERENCE TO RELATED APPLICATIONS

This application is a continuation-in-part application of application, U.S. Ser. No. 237,141, filed on Aug. 26, 1988, now abandoned; which is a divisional of application, U.S. Ser. No. 019,413, filed on Feb. 26, 1987, now U.S. Pat. No. 4,778,826, issued on Oct. 18, 1988; which is a divisional of application, U.S. Ser. No. 781,214, filed Sept. 26, 1985, now U.S. Pat. No. 4,654,458, issued on Mar. 31, 1987. The co-pending parent application is hereby incorporated by reference herein and is made a part hereof, including but not limited to those portions which specifically appear hereinafter.

BACKGROUND OF THE INVENTION

1. Field of the Invention

This invention relates generally to a method for converting a lower molecular weight alkane to a higher molecular weight hydrocarbon and more particularly concerns a method for converting a lower molecular weight alkane to synthesis gas and then converting the synthesis gas to higher molecular weight materials in the presence of a Fischer-Tropsch catalyst.

This invention also relates generally to temperature control or regulation and, more particularly, to methods and apparatuses for regulating temperature in a heterogeneous reaction system.

2. Description of the Related Art

A major source of lower molecular weight alkanes is natural gas. Lower molecular weight alkanes are also present in coal deposits and are formed during numerous mining operations, in various petroleum processes, and in the above- or below-ground gasification or liquefaction of coal, tar sands, oil shale, and biomass.

It is highly desirable to convert lower molecular weight alkanes to more valuable, higher molecular weight materials and a number of attempts to do so have been reported. Because of the high energy costs associated with heating reactants, it is highly desirable that an exothermic process be employed to effect this conversion. One such exothermic process is the exothermic partial oxidation of the lower molecular weight alkane with oxygen to form synthesis gas, which is subsequently converted in a Fischer-Tropsch operation to a higher molecular weight material.

Typical features of many of the reported processes involving the formation of synthesis gas by the partial oxidation of a lower molecular weight alkane and the subsequent conversion of the synthesis gas by a Fischer-Tropsch operation are the use of relatively high pressures in both the synthesis gas formation and conversion steps, the separation of oxygen from air for use in the synthesis gas formation step, and the use of separate heat exchangers, in addition to the synthesis gas formation reactor, to heat the reactants for the synthesis gas formation and to cool the resulting synthesis gas to a temperature range that is suitable for the subsequent synthesis gas conversion reaction.

Furthermore, typically the Fischer-Tropsch conversion of synthesis gas is effected in the absence of an inert diluent such that, as a result of the high partial pressure of synthesis gas and the high rate of synthesis gas conversion, less desirable products such as methane, waxy hydrocarbons and alcohols are formed, and hot spots develop and waxy or carbonaceous deposits are formed in the catalyst bed which reduce catalyst activity. In addition, while the simultaneous meeting of relatively high activity and selectivity targets; for example, 80+% for each, in the conversion of synthesis gas can relatively easily be attained with small, isothermal laboratory reactors, process development of commercial reactors capable of achieving these targets while handling the large amounts of heat generated during the synthesis gas conversion, e.g., a reactor operating at near isothermal operation, has proven more elusive.

Several approaches to commercial reactor design have, in the past, been utilized to control exothermic reactions while approximating isothermal operation. One such approach has been to maintain the reaction in relatively long, narrow tubes with bundles of these tubes being maintained in a heat transfer medium. Thus, in such a reactor design the reaction occurs within the tubes and the tubes contain any reaction catalyst. A second approach, frequently practiced in conjunction with the first, is to use recycle. A third approach is to conduct the synthesis gas conversion in stages, where only partial conversion occurs in the first stage, and after separation of the products, the remaining unreacted synthesis gas is either converted in a second stage or recycled to the first stage. In either case, high capital costs and operating expenses are involved.

However, such features are not desirable in an economical commercial process. It is highly desirable in a commercial process involving the partial oxidation of a lower molecular weight alkane to form synthesis gas and the subsequent conversion of the synthesis gas by a Fischer-Tropsch operation to effect the synthesis gas formation in a single reactor under at least partially adiabatic conditions such that the exothermic heat generated is utilized in heating the subsequently introduced reactants to the desired reaction temperature. It is also highly desirable to employ air as the source of oxygen in the synthesis gas formation step and to thereby replace the relatively difficult and costly separation of oxygen from air with the relatively simpler and less expensive separation of nitrogen from the final hydrocarbon products and to thereby also utilize the nitrogen component of the air employed in the synthesis gas formation step as an inert diluent in the synthesis gas conversion step to sweep the reactants and products through the reactor, to facilitate the removal of heat generated in the exothermic synthesis gas conversion, and to thereby avoid the development of hot spots and the formation and deposition of waxy or carbonaceous materials in the catalyst bed of the synthesis gas conversion reactor. It is also highly desirable that the Fischer-Tropsch conversion of synthesis gas occur at a high conversion and at a relatively low pressure and with a reduced formation of higher molecular weight hydrocarbon waxes and oxygenates.

OBJECTS OF THE INVENTION

It is therefore a general object of the present invention to provide an improved method for converting a lower molecular weight alkane to synthesis gas and then for converting the synthesis gas to a higher molecular weight hydrocarbon in the presence of a Fischer-Tropsch catalyst, which method overcomes the problems of prior art methods and affords the aforementioned desired characteristics.

More particularly, it is an object of the present invention to provide an improved aforesaid method which employs air as the source of oxygen for the conversion of the lower molecular weight alkane to synthesis gas and as the source of nitrogen as an inert diluent in the conversion of the resulting synthesis gas.

It is a further object of the present invention to provide an improved aforesaid method wherein the heating of the lower molecular weight alkane and air, the exothermic conversion of the alkane with oxygen to form synthesis gas, and the cooling of the resulting synthesis gas product to a temperature desired for the subsequent synthesis gas conversion are effected within a packed bed of particles within a single reactor, wherein the heat generated in the synthesis gas formation is utilized to heat the incoming reactants to a temperature where the synthesis gas formation reaction occurs.

It is another object of the present invention to provide an improved aforesaid method wherein the higher molecular weight hydrocarbon product is formed from the synthesis gas at high conversion and selectivity in a single-pass, single-stage operation at a low pressure and in the presence of an inert diluent to sweep the reactants and products through the reaction zone and thereby to avoid the development of hot spots in the reaction zone and control the rate of reaction.

It is another object of the present invention to provide an improved reactor apparatus useful in regulating temperature in a heterogeneous reaction system.

It is a further object of the present invention to provide an improved method of regulating temperature in a heterogeneous reaction system.

Other objects and advantages of the invention will become apparent upon reading the following detailed description and appended claims, and upon reference to the accompanying drawings.

SUMMARY OF THE INVENTION

According to the invention, an improved method for converting at least one feedstock alkane containing from one to three carbon atoms to a more valuable, higher molecular weight hydrocarbon, comprises: (a) passing a reaction mixture comprising the feedstock alkane and air at a pressure in the range of from about 1 to about 50 pounds per square inch gauge through an elongated first reactor packed with a bed of particles, wherein the particles are at a substantially higher temperature than is the incoming reaction mixture and wherein: (1) in the upstream zone of the first reactor, the reaction mixture is contacted with the relatively hotter particles therein, the temperature of which particles increases in the direction of gas flow, whereby the reaction mixture is heated to a temperature at which the reaction of the feedstock alkane with oxygen to form synthesis gas commences, and the particles therein are cooled by contact with the relatively cooler reaction mixture; (2) in the middle zone of the first reactor, the feedstock alkane and oxygen react exothermally to form a gaseous product stream comprising carbon monoxide, hydrogen, and nitrogen and to generate sufficient heat that the temperature of the product stream therein is raised; and (3) in the downstream zone of the first reactor, the product stream is contacted with the relatively cooler particles therein, the temperature of which particles decreases in the direction of gas flow, whereby the product stream is cooled to, and exits the first reactor at, a temperature in the range of from about 100° C. to about 500° C. and the particles therein are heated; and (b) passing the gaseous product stream from the first reactor through an elongated second reactor packed with a bed of particles comprising a Fischer-Tropsch catalyst, maintained at a pressure in the range of from about 1 to about 50 pounds per square inch gauge and cooled to maintain the temperature therein in the range of from about 160° C. to about 240° C., to form a gaseous product stream comprising aliphatic products having higher molecular weights than the feedstock alkane.

Also according to the present invention, a reactor apparatus useful in regulating temperature in a heterogeneous reaction system comprises an elongated tube reactor packed with a bed of solid particles through which a reactant fluid phase of the heterogeneous reaction system is passed. A plurality of heat transfer medium passage means are imbedded in the bed of solid particles with the passage means being substantially transverse to reactant flow through the reactor. Adjacent passage means are in spaced relationship relative to each other about the longitudinal axis of the reactor.

In addition to the above-described apparatus, the invention comprehends methods of temperature regulation in a heterogeneous reaction system.

BRIEF DESCRIPTION OF THE DRAWINGS

FIG. 2 illustrates the temperatures at each such point at various times during a 30-minute cycle during which the flow of gas is from the first end to the second end of the reactor, and FIG. 3 illustrates the temperatures at each such point at various times during the next 30-minute cycle during which the direction of gas flow is reversed and the gas flows from the second end to the first end of the reactor.

FIG. 6 is a simplified schematic drawing of the reactor apparatus of the present invention, according to a typical embodiment.

FIG. 7 is a top view of serpentine tube shape heat transfer medium passage tube according to a typical embodiment of the invention.

FIG. 8 is a top view of a sandwiched spiral coil comprising two spiral coiled proportions interposed in the same tube actual plane with the two proportions being connected with an S-shaped connector, heat transfer medium tube according to a difficult embodiment of the invention.

FIG. 9 is a cross sectional partial view of the reactor apparatus of FIG. 6 in the absence of solid particle packing and taken along the line 9—9.

It should be understood that the embodiments are sometimes illustrated in FIGS. 1-9 by graphic symbols and diagrammatic representations. In certain instances, details which are not necessary for an understanding of the present invention or which render other details difficult to perceive may have been omitted. It should be understood, of course, that the invention is not necessarily limited to the particular embodiments illustrated herein.

DETAILED DESCRIPTION OF THE DRAWINGS INCLUDING PREFERRED EMBODIMENTS

Figure 1:
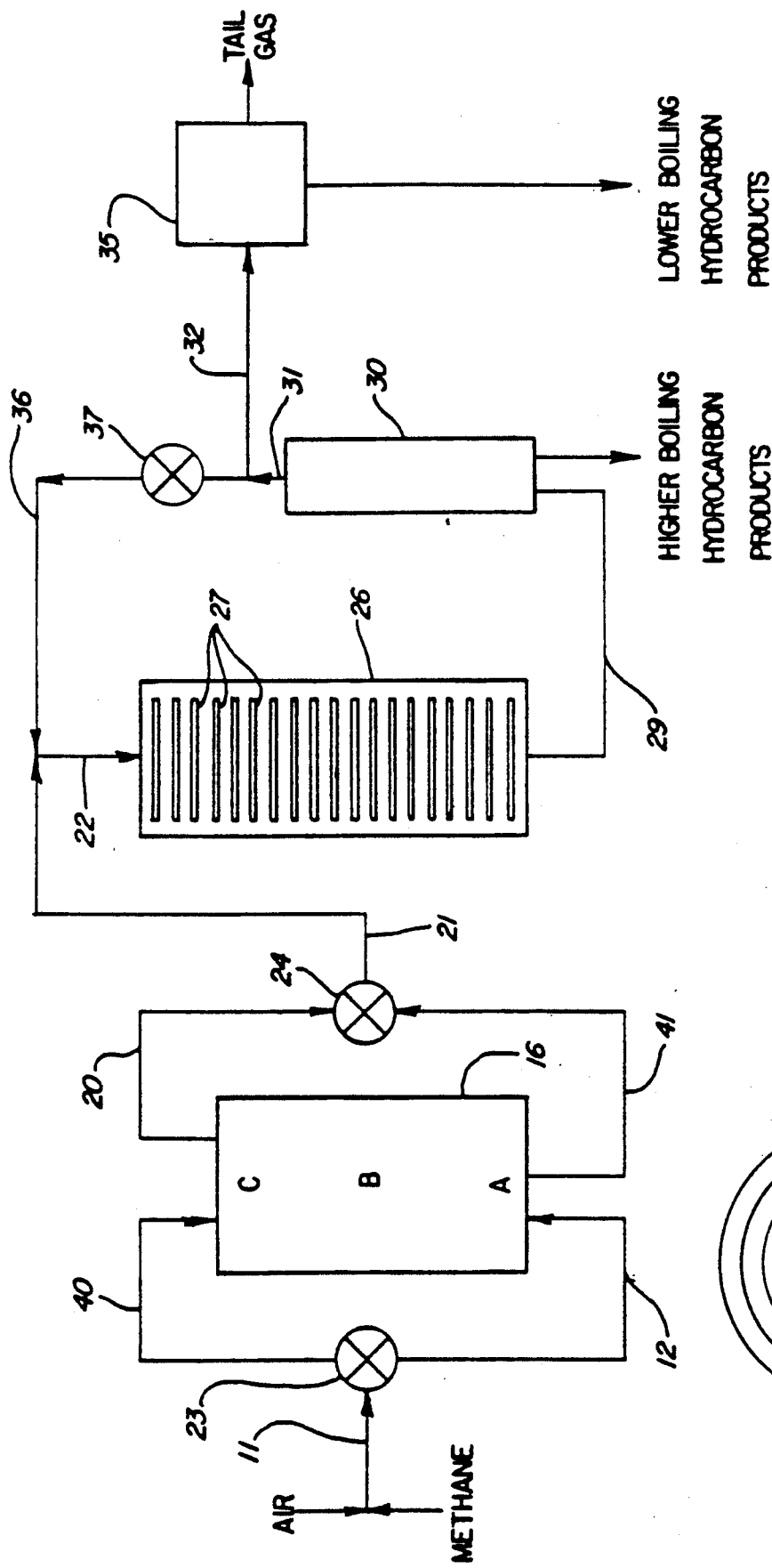
FIG. 1 is a schematic illustration of a preferred embodiment of the present invention in which: a reaction mixture of methane and air is introduced into one end of a first reactor packed with a bed of particles whose temperature profile is substantially higher than the temperature of the incoming gas stream and which is maintained at or near atmospheric pressure; as the gas stream proceeds through the bed of particles, the gas stream is heated to a temperature at which methane reacts exothermally with oxygen to form a product stream comprising synthesis gas and nitrogen and having a substantially higher temperature as a result of the exothermic heat generated; before the product stream leaves the first reactor, its temperature is reduced by contact with the cooler particles in the downstream portion of the first reactor; the product stream is then introduced into a second reactor containing a bed of particles comprising a Fischer-Tropsch catalyst where the synthesis gas reacts at a controlled temperature and reaction rate and at high conversion to form at high selectivity higher molecular weight hydrocarbon products; at least a portion of the highest boiling components of the resulting high molecular weight hydrocarbon products are separated from the product stream in a first separator; and at least a portion of the remaining high molecular weight hydrocarbon products are separated in a second separator from at least a portion of the remaining product stream from the first separator.

Turning first to FIG. 1, there is shown schematically a preferred embodiment of the method of this invention. Methane, illustrative of a feedstock comprising at least one alkane containing from 1 to 3 carbon atoms, is mixed with air, as the source of the reactant oxygen and of the inert diluent nitrogen, and the resulting mixture is introduced through lines 11 and 12 into a first reactor 16 packed with a bed of particles whose temperature is substantially higher than the temperature of the incoming gas stream. The temperature of the reaction mixture before entering the reactor 16 is in the range of from about 0° C. to about 100° C. As it passes through the zone A in the reactor 16, the gas stream is raised to a temperature at which the conversion of methane by reaction with oxygen to form synthesis gas commences, by contact with the relatively hotter particles in zone A. The oxidation of methane proceeds exothermally, and preferably substantially to completion, in the middle zone B of the reactor 16 to form a product stream comprising synthesis gas—that is, carbon monoxide and hydrogen—and nitrogen, and generates sufficient heat that the temperature of the product stream in the middle zone B of the reactor 16 is raised. As it passes through the zone C in the reactor 16, the product mixture is cooled to a temperature in the range of from about 150° C. to about 500° C. by contact with the relatively cooler particles therein. Also as a result of this heat transfer from the product stream to the particles in the zone C of the reactor 16, the temperature of the particles in the zone C of the reactor 16 is raised.

The effluent from the reactor 16 is a gaseous product stream comprising synthesis gas and nitrogen and is introduced through the lines 20, 21, and 22 into a second reactor 26, where it is contacted with a suitable synthesis gas conversion catalyst under synthesis gas conversion conditions to form hydrocarbon products having higher molecular weights than the feedstock alkane. The temperature in the reactor 26 is maintained in the range of from about 160° C. to about 240° C. by means of cooling coils 27 disposed within the bed of particles therein. A preferred embodiment of the cooling coils 27 is illustrated in greater detail in FIG. 4. The effluent from the reactor 26 comprises the higher molecular weight hydrocarbon products, nitrogen, and any remaining unreacted synthesis gas and is passed through line 29 to a first separator 30 where the separation of a higher boiling fraction of the products produced in the reactor 26 is effected. The remaining gaseous product mixture is withdrawn in lines 31 and 32 from the first separator 30 and introduced into a second separator 35 where lower boiling, normally liquid products and at least a portion of the gaseous hydrocarbon products are separated. The gaseous effluent from the second separator 35 comprises nitrogen and any remaining normally gaseous hydrocarbon products and unreacted synthesis gas.

It should be understood that FIG. 1 illustrates merely one preferred embodiment of the method of this invention and that the present invention is not limited to the particular embodiment illustrated in FIG. 1.

Thus, in the method of the present invention, the temperature of the particles in the zone A of the reactor 16 is lowered as a result of contact thereof with the relatively cooler incoming reaction mixture, and the temperature of the particles in the zone C of the reactor 16 is raised as a result of contact thereof with the relatively hotter product mixture. In addition, during the cooling of the reaction mixture by contact with the particles in the zone C of the reactor 16, carbonaceous materials commonly called "coke" can form and deposit on the relatively cooler particles in the zone C. The build-up of coke deposits on the particles in the zone C of the reactor 16 results in an increased pressure drop through the bed of particles in the reactor 16, and, with time, can ultimately necessitate the run to be terminated for removal of the coke deposits or replacement of the coked particles in the zone C of the reactor 16.

In order to avoid this problem, in a preferred embodiment of the method of this invention, the direction of gas flow through the reactor 16 is reversed cyclically such that, in alternate cycles, the zone A of the reactor 16 is employed as the upstream zone and the zone C is employed as the downstream zone, and in the intervening cycles, the zone C is employed as the upstream zone and the zone A is employed as the downstream zone. Typically, a cycle is allowed to proceed for from about 5 minutes to about 5 hours, preferably from about 30 to about 60 minutes, before the direction of gas flow through the reactor is reversed.

Thus, the particles which are employed to cool the product mixture and which are heated by contact with the product mixture in one cycle serve as a source of heat to raise the temperature of the incoming reaction mixture in the next cycle. In this sense; the bed of particles in the reactor 16 is operated in the method of this invention adiabatically or at least partially adiabatically, with exothermic heat generated during one cycle being retained in the particles in one end of the reactor 16 and being employed to heat the incoming gas in the next cycle. Furthermore, by cyclically reversing the direction of gas flow in the reactor 16, any coke deposits formed on the particles during the cooling of the product mixture in one cycle are removed by reaction with oxygen during the heating of the incoming reaction mixture in the next cycle. Thus, it is possible to essentially eliminate the problem of the development of a high pressure drop in the reactor 16 and to avoid terminating a run because of the high pressure drop resulting from coke deposits on the particles in the reactor 16.

Systems of the type illustrated in FIG. 1 have been continually operated with cyclical reversal of the direction of gas flow through the reactor 16 for over 6 months, with no additional heat input required after the particles were initially heated at the commencement of the run (as described hereinbelow) and without coke build-up on the particles in the reactor 16. By contrast, when the direction of gas flow through the reactor 16 is not reversed cyclically, an external source of heat is necessary to maintain the particles in the upstream and middle zones as a source of heat to raise the temperature of the incoming reaction mixture, and as a cooling means to cool the product stream to the desired exit gas temperature, and the high pressure drops which may develop in the reactor 16 as a result of the build-up of coke on the particles in the downstream zone of the reactor 16 may necessitate termination of the run after only several days. For example, in a pilot plant run in which the direction of gas flow was not reversed, the pressure drop over the length of the reactor increased gradually as a result of the build-up of coke on the packed bed therein, such that discontinuance of the run once every about 2 to about 6 days was necessary in order to remove the coke deposits and to maintain the pressure drop within the desired limits. By contrast, by periodically reversing the direction of gas flow through the reactor, continuous runs of over 6 months were achieved without the need to remove coke deposits.

In the embodiment illustrated in FIG. 1, during an alternate cycle, the flow of the reaction mixture is, as described hereinabove, through the lines 11 and 12 and through the reactor 16 from the upstream zone A through the middle zone B to the downstream zone C and then from the reactor 16 through the lines 20 and 21. During an intervening cycle, the valves 23 and 24 are switched so as to direct the flow of the reaction mixture through the lines 11 and 40 and through the reactor 16 from the upstream zone C through the middle zone B to the downstream zone A and then from the reactor 16 through the lines 41 and 21.

Generally, a suitable feedstock for the method of this invention comprises at least one of methane, ethane and propane, and preferably comprises methane. Thus, a suitable feedstock for the method of this invention comprises natural gas, gases formed during mining operations, in petroleum processes, or in the above- or below-ground gasification or liquefaction of coal, tar sands, oil shale, and biomass. Air is employed both as the source of oxygen required for the generation of synthesis gas and as the source of nitrogen as the inert diluent in the method of this invention. If desired, the air could be enriched with oxygen or, if too exothermic, diluted with nitrogen or other inert gas. The mole ratio of oxygen to each carbon atom of the feedstock alkane containing from 1 to 3 carbon atoms introduced into the synthesis gas generation reactor in the method of this invention is in the range of from about 0.5 to about 0.8, preferably from about 0.52 to about 0.7.

The synthesis gas generation reactor is sized to provide a sufficient residence time, calculated on the basis of empty bed volume and gas volume at the maximum reactor temperature, in the middle zone of the reactor for the feedstock alkane to be exothermally, and preferably substantially completely converted by reaction with oxygen to form synthesis gas, and to provide sufficient residence times in the upstream and downstream zones to permit the reaction mixture to be heated in the inlet zone from its initial temperature to a temperature where the aforesaid conversion commences and to permit the product mixture to be cooled to a desired exit gas temperature, respectively, as described herein. For a given reactor, the lengths of the upstream and downstream zones are a function of where the reaction mixture is being heated to the temperature at which the conversion commences and where the product mixture is being cooled, and the intervening length is the middle zone. Generally, the residence time of gas in the middle zone of the reactor is in the range of from about 0.025 to about 10 seconds.

To commence a run, the particles in the synthesis gas generation reactor are heated by any suitable conventional means, for example, electrically or by direct firing, such that the particles in the upstream zone are sufficiently hot to heat the incoming reaction mixture to a temperature where the aforesaid oxidation of the feedstock alkane commences and such that the particles in the downstream zone are sufficiently cool to cool the product stream to the desired exit gas temperature. The initial temperature profile of the particles in the reactor is such that the temperature of the particles increases in the direction of gas flow from the inlet to the middle zone and then decreases in the direction of gas from the middle zone to the outlet of the reactor. Depending on the conditions of operation, there may be a single maximum temperature or a plurality of maximum temperatures in the middle zone of the reactor.

Then the feed gas is caused to flow in one direction through the particles in the synthesis gas generation reactor. Generally, the reaction mixture is at a temperature in the range of from about 0° C. to about 100° C. as it enters the synthesis gas generation reactor and is heated to the temperature at which the synthesis gas generation reaction commences, by contact with the substantially hotter particles in the upstream zone of the reactor. If necessary or desired, heating or cooling coils are disposed or imbedded in the particles in the upstream zone of the synthesis gas generation reactor to provide supplemental control of the temperature of the particles and gas therein. As a result of the heat transfer from the particles in the upstream zone to the incoming reaction mixture, such particles at the inlet are cooled to a temperature in the range of from about 100° C. to about 300° C.

As used in the present context, the term "commencement" of the synthesis gas generation reaction means the occurrence of the synthesis gas generation reaction at a sufficiently high rate that sufficient sensible exothermal heat is generated to effect a measurable increase in the temperature of the gas passing through the reactor. The synthesis gas generation reaction commences when the reaction mixture is heated to a temperature in the range of from about 500° C. to about 900° C., preferably in the range of from about 650° C. to about 850° C.

If a catalyst for the synthesis gas generation reaction is employed in the middle zone of the synthesis gas generation reactor, the synthesis gas generation reaction commences at a lower temperature than if the catalyst were not employed.

In the middle zone of the synthesis gas generation reactor, the conversion of the feedstock alkane by reaction with oxygen occurs exothermally, and preferably substantially to completion, to form a product stream comprising carbon monoxide, hydrogen and nitrogen and to generate sufficient heat that the temperature of the product mixture in the middle zone of the reactor is raised to a temperature in the range of from about 800° C. to about 1,500° C. The partial pressures of either or both of the feedstock alkanes and oxygen in the gaseous effluent from the synthesis gas formation reaction are preferably substantially zero.

Before exiting from the synthesis gas generation reactor, the product stream passes through the relatively cooler particles in the downstream zone of the reactor where it is cooled by contact with the relatively cooler particles therein to a temperature, at which the synthesis gas generation reaction does not proceed at a high enough rate to generate sufficient exothermic heat to increase or maintain constant the temperature of the gas passing through the reactor. Thus, the product stream is cooled to a temperature in the range of from about 25° C. to about 500° C., preferably to a temperature in the range of from about 150° C. to about 450° C., and more preferably to a temperature in the range of from about 175° C. to about 250° C. It is highly preferred in the method of this invention that the product stream exits from the synthesis gas generation reactor at substantially the temperature desired for this stream as it enters the synthesis gas conversion reactor. Thus, if necessary or desired, heating or cooling coils are disposed in the particles in the outlet portion of the synthesis gas generation reactor to provide supplemental control of the temperature of the particles and gas therein. In the alternative or in addition, a separate heat exchanger can be employed downstream of the synthesis gas generation reactor and upstream of the synthesis gas conversion reactor to adjust the temperature of the product stream from the synthesis gas generation reactor to the temperature desired for the synthesis gas conversion reaction.

The synthesis gas generation of the method of this invention is performed under a total pressure in the range of from about 1 to 50 pounds per square inch gauge, and preferably in the range of from about 1 to about 15 pounds per square inch gauge. In general, only sufficient pressure is necessary to overcome any back pressure in the synthesis gas generation reactor and to move gases through such reactor.

The synthesis gas formation step in the method of this invention is performed preferably at a space velocity, calculated at 0° C. and one atmosphere absolute, of from about 25 to about 5,000 cubic centimeters of total gas comprising the aforesaid feedstock alkane per hour per cubic centimeter of particles in the synthesis gas formation reactor and more preferably at a space velocity of from about 50 to about 2,500 cubic centimeters of total gas comprising the aforesaid feedstock alkane per hour per cubic centimeter of particles in the synthesis gas formation reactor. The synthesis gas formation step is performed at a space velocity, calculated for a reaction pressure of one atmosphere absolute, more preferably of from about 500 to about 20,000, and most preferably of from about 1,000 to about 10,000, cubic centimeters of the aforesaid total gas per hour per cubic centimeter of particles in the middle zone of the synthesis gas formation reactor where the synthesis gas is formed.

The particles employed in the synthesis gas formation reactor in the method of this invention comprise refractory particles. Suitable refractory materials that are generally inert under the conditions employed include the following: coarse sand, pebbles, stone, crushed rock, and crushed ores. In the alternative and preferably, the refractory material comprises an amorphous refractory inorganic oxide comprising an oxide of an element from Group IIA, IIIA, IIIB, IVA, or IVB of the Periodic Table. More preferably, the amorphous refractory inorganic oxide employed in the synthesis gas formation step of the method of this invention comprises zirconia, silica, alumina, silica-alumina, silica-stabilized alumina, phosphated alumina, silica-stabilized phosphated alumina, alumina-aluminum phosphate, boria-alumina, magnesia-alumina, boria, magnesia, titania, or mixtures thereof.

The particles employed in the synthesis gas formation reactor can also comprise materials which catalyze the formation of synthesis gas. For example, although most of the aforesaid refractory inorganic oxides are inert when employed as the particles in the synthesis gas formation reaction of the method of this invention, some—for example, zirconium-, magnesium-, platinum group metal (platinum, palladium, rhodium, iridium, osmium, and ruthenium)-, nickel- or copper-containing materials catalyze the formation of synthesis gas in the method of this invention and can be components of the particles employed in the synthesis gas formation reaction. Such catalytic materials can be employed either in the form of the elemental metal or its oxide. The use of such a catalyst in the synthesis gas generation reaction is beneficial because it permits the use of a molar ratio of oxygen-to-each carbon atom of the feedstock alkane as low as 0.5 and allows the catalyzed synthesis gas formation to take place at a relatively low temperature such that, even with the heat generated exothermally, the maximum temperature of the product stream in the reactor is less than about 1,100° C. By contrast, the uncatalyzed synthesis gas formation reaction generally requires a molar ratio of oxygen-to-each carbon atom of the feedstock alkane of above about 0.6 and generally takes place at higher temperatures such that, with the heat generated exothermally, the maximum temperature of the product stream is 1,200° C.–1,500° C.

The aforesaid catalytic materials can be employed as the refractory particles themselves or as components incorporated into the refractory particles. Thus, at least one of a catalytic material such as zirconium, magnesium, an elemental platinum group metal(platinum, palladium, rhodium, iridium, osmium, and ruthenium), nickel, copper, an oxide of any thereof or a mixture thereof can be incorporated into a support of a different material—that is, a material other than zircoia or magnesia— comprising one of the aforesaid inert refractory materials, preferably an oxide of an element of Group IIA, IIIA, IIIB, IVA, or IVB of the Periodic Table, more preferably alumina, silica, silica-alumina, silica-stabilized alumina, phosphated alumina, silica-stabilized phosphated alumina, boria, titania, boria-alumina, alumina-aluminum phosphate, or mixtures thereof. When the catalyst comprises a support, the catalyst typically comprises from about 0.01 to about 98 weight percent of the catalytic component, calculated as its oxide and based on the weight of the catalyst. The preferred concentration of the catalytic component in the supported catalyst generally depends on the particular catalytic component, as illustrated hereinbelow.

The particles in the synthesis gas generation reaction can suitably comprise a homogeneous mixture of or separate layers of inert particles and particles comprising an aforesaid catalytic component. Preferably, the particles employed in the upstream and downstream zones of the synthesis gas generation reactor are inert, and the particles in the middle zone comprise an aforesaid catalytic component or comprise a mixture of inert particles and particles comprising an aforesaid catalytic component.

The catalysts preferably employed in the synthesis gas formation step of the method of this invention are either commercially available or can be prepared by any conventional technique for incorporation thereof into or onto an aforesaid inert refractory material. For example, any convenient, conventional technique can be employed for this purpose, such as impregnation from solution, vapor deposition, intimate physical mixing and the like. For example, a soluble compound of zirconium, magnesium, nickel, copper, or a platinum group metal can be added to a sol or gel of an aforesaid amorphous refractory inorganic oxide. This composition is then thoroughly blended into the sol or gel mixture and is subsequently co-gelled by the addition of dilute ammonia solution. The resulting co-gelled material is then dried. In another method of preparation, the refractory inorganic oxide is gelled, dried, and cooled, and the resulting material is then impregnated with one or more solutions of a soluble compound of zirconium, magnesium, nickel, copper, or a platinum group metal. The support containing the metal compound or precursor thereof can then be calcined, thereby forming the zirconia, magnesia, or oxide of nickel, copper or platinum group metal. The calcination conditions employed are preferably a temperature of from about 500° C. to about 1,050° C. for from about 2 hours to about 36 hours and more preferably calcination in air at a temperature of from about 950° C. to about 1,050° C. for from about 4 hours to about 20 hours.

In one example of the synthesis gas generation reaction performed in accordance with the method of this invention, a 44-inch long, vertically disposed reactor having an internal diameter of 2.5 inches was packed with inert alumina spheres (Denstone 99 from Norton Company) having an average diameter of about 0.25 inch and contained a void volume of 0.12 cubic foot. The particles were initially heated by external electric heaters such that the particles within the 20-inch long middle zone of the reactor were at temperatures in the range of from about 800° C. to about 1,400° C. and the particles on both sides of this middle portion were at temperatures in the range of from about 100° C. to about 800° C., with the temperature increasing from the inlet to the highest temperature in the middle zone and then decreasing to the outlet. The electric heaters were employed throughout the run to maintain the reactor walls at approximately the same temperatures as were the particles inside the reactor.

A feed stream of 23 volume percent of methane and 77 volume percent of air was introduced at 25° C. into the top end of the reactor. The methane and air were introduced at flow rates of 923 and 3092 standard cubic centimeters per minute, respectively. The space velocities of the volume of total gas per hour per volume of all particles in the reactor and per volume of particles in the middle zone of the reactor were 100 and 2,450 hr$^{-1}$, respectively, calculated at 0° C. and atmospheric pressure absolute. Under these conditions, a particle bed length of about 8 inches corresponded to a residence time therein for the gas of about 0.6 second. The direction of flow of gas through the reactor was reversed every 5 minutes.

After about 6 hours of operation, the pressure drop over the length of the bed of particles in the reactor was 0.2 pound per square inch gauge, and the total gas pressure at the inlet of the reactor was 1.3 pounds per square inch gauge. The maximum temperature of the products formed by the exothermic synthesis gas generation reaction was 1306° C. in the middle zone of the bed of particles in the reactor. At this duration of operation, the product stream exiting from the bottom end of the reactor had the following composition: 0.8 mole percent of methane; undetectable amounts of oxygen; 47.9 mole percent of nitrogen; 28.1 mole percent of hydrogen; 14.6 mole percent of carbon monoxide; 1.9 mole percent of carbon dioxide; 6.2 mole percent of water; and 0.5 mole percent of argon.

In a second example of the synthesis gas generation reaction performed in accordance with the method of this invention, a 38-inch long, horizontally disposed reactor having an internal diameter of 2.5 inches was employed. In one set of runs, the reactor was packed throughout with inert alumina spheres having an average diameter of 0.25 inch, and in a second set of runs, the inert spheres in the 24-inch long middle zone of the reactor were replaced by pellets having catalytic properties and comprising 98 weight percent of zirconia and 2 weight percent of alumina and having an average length of 0.25 inch and an average width of 0.125 inch. In all cases, the reactor contained a void volume of 772 cubic centimeters. The particles were initially heated by an external electric heater such that the particles within the middle 24 inches of the reactor were at temperatures of about 800° C. to about 1,000° C. and the particles on both sides of this middle zone were at temperatures in the range of from about 100° C. to about 800° C., with the temperature increasing from the inlet to the highest temperature in the middle zone and then decreasing to the outlet.

A feed stream containing 26 volume percent of methane and 74 volume percent of air was introduced at 25° C. into one end of the reactor. The methane and air were introduced at flow rates of 428 and 1,227 standard cubic centimeters per minute, respectively. Under these conditions the residence time therein for the gas was about 6 seconds.

After several hours of operation, the pressure drop over the length of the bed of particles in the reactor was 0.1 pound per square inch gauge, and the total gas pressure at the inlet of the reactor was 1 pound per square inch gauge. The results of these runs are presented in Table 1 hereinbelow and illustrate the differences in the degree of conversion of methane, the yield of carbon monoxide, and the hydrogen-to-carbon monoxide mole ratio that resulted from the use of particles having a catalytic component in the reactor.

Thus, at the reaction temperature of about 1,000° C., the degree of conversion of methane, the yield of carbon monoxide and the molar ratio of hydrogen to carbon monoxide produced were higher when the layer of particles having a component which catalyzes the synthesis gas formation was employed. At lower temperatures, the molar ratios of hydrogen to carbon monoxide produced were higher when particles containing a catalytic component were employed.

In another example of the synthesis gas generation reaction of the method of this invention, a 44-inch long vertically disposed reactor having an internal diameter of 2.5 inches was packed, in the top 18 inches and bottom 18 inches thereof, with inert alumina (Denstone 99) spheres having an average diameter of about 0.25 inch and, in the middle 8 inches thereof, with catalyst particles comprising 8 weight percent of nickel oxide on a spherical alumina support having an average diameter of 0.375 inch. The void volume of the bed of particles in the reactor was 0.12 cubic foot. The particles were initially heated by electric heaters such that the particles at various lengths along the axis of the reactor were approximately at the initial temperatures illustrated in FIG. 2.

A feed stream comprising 28 volume percent of methane and 72 volume percent of air was introduced at about 25° C. into the top end of the reactor. The methane and air were introduced at flow rates of 3,359 and 8,754 standard cubic centimeters per minute, respectively. The space velocities of the volume of total gas per hour per volume of all particles in the reactor and per volume of catalyst particles in the middle zone of the reactor were 222 and 4,608 hr$^{-1}$, respectively, calculated at 0° C. and atmospheric pressure absolute. Under these conditions, a particle bed length of about 8 inches corresponded to a residence time therein for the gas of about 0.28 second. The pressure drop over the length of the bed of particles in the reactor was 0.2 pound per square inch gauge, and the pressure of the gas at the inlet of the reactor was 1.4 pounds per square inch gauge. The direction of the flow of gas through the reactor was reversed every 30 minutes.

Figure 2:
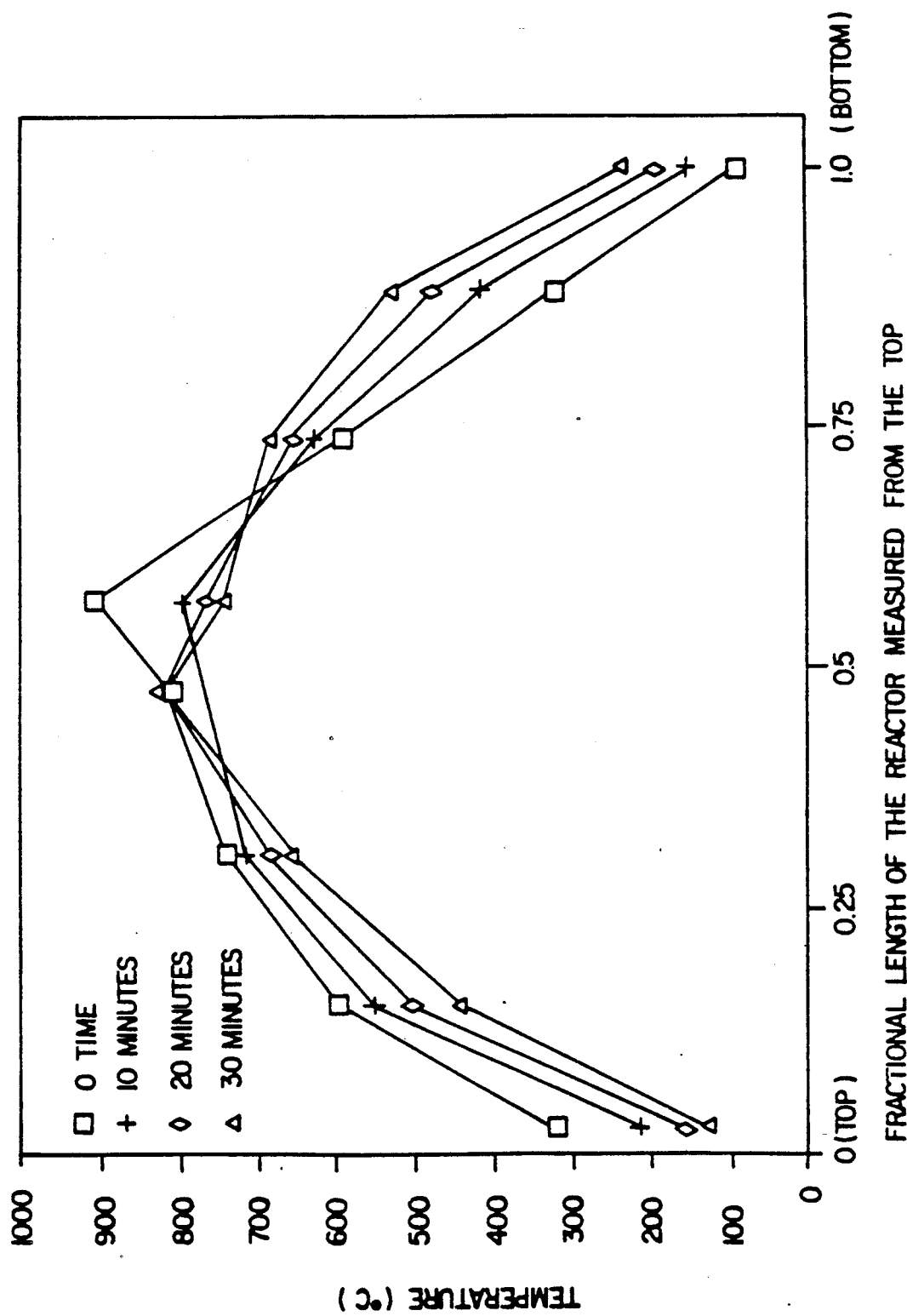
FIGS. 2 and 3 illustrate the temperatures at various points along the length of the bed of particles employed in the reactor for the synthesis gas generation reaction in the preferred method of the present invention.
Figure 3:
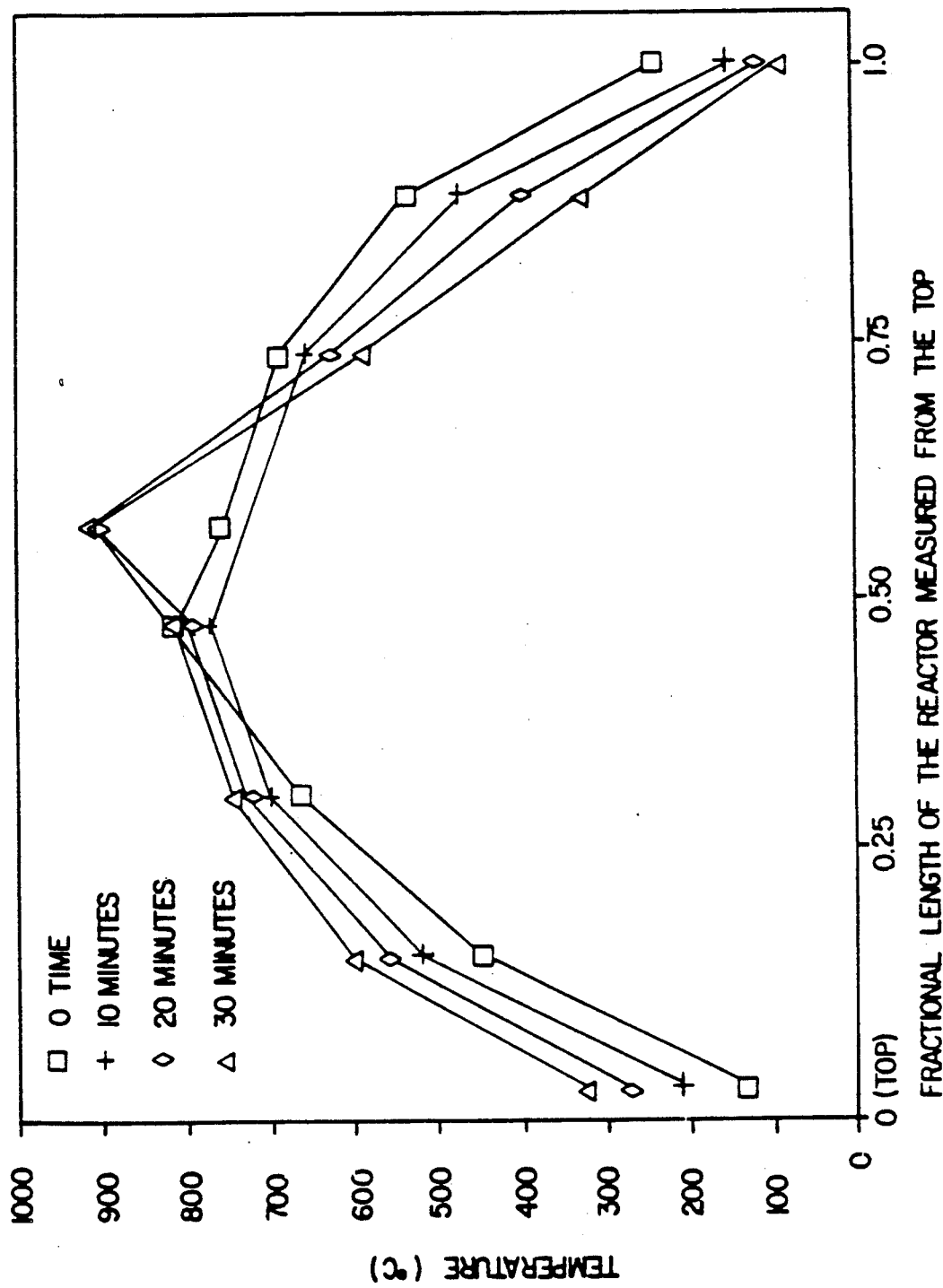

FIGS. 2 and 3 contain plots of the measured temperatures of the particles in the bed at various points along the length of the reactor versus the distance of each such point from the top of the bed, the location of each such point along the length of the bed reported as "X", the fraction of the full length of the bed measured from the top of the bed. Thus, in the X-axis of FIGS. 2 and 3, zero represents a point located at the top of the bed, 1 represents a point located at the bottom of the bed, and 0.5 represents a point midway between the top and bottom of the bed.

The temperature profiles shown in FIG. 2 were measured when the gas flowed downwardly from top (X=0) to bottom (X=1) through the reactor, and the temperature profiles shown in FIG. 3 were measured when the gas flowed upwardly from the bottom (X=1) to the top (X=0) through the reactor. In each of FIGS. 2 and 3, the temperature profile measured at time zero represents the temperatures measured immediately after the direction of gas flow was reversed and the direction of flow became downward for FIG. 2 and upward for FIG. 3.

Thus, as illustrated by the temperature profiles in FIG. 2, when the feed gas flowed downwardly through the reactor, the temperature of the particles at the inlet or top (X=0) of the reactor decreased from 320° C. at time zero to 130° C. at 30 minutes immediately before the direction of flow was reversed, and the temperature of the particles at the outlet or bottom (X=1) of the reactor increased from 100° C. at time zero to 260° C. at 30 minutes. As illustrated by the temperature profiles in FIG. 3, when the direction of flow of the feed gas was then reversed such that the feed gas flowed upwardly through the reactor, the temperature of the particles at the inlet or bottom (X=1) of the reactor then decreased from 260° C. at time zero to 100° C. at 30 minutes, and the temperature at the outlet or top (X=0) increased from 130° C. at time zero to 320° C. at 30 minutes. The steady state results of this run were as follows: 99 weight percent conversion of methane; 100 weight percent conversion of oxygen; 98.2 weight percent yield of carbon monoxide; and a product stream containing 0.20 weight percent of methane, 19.23 weight percent of carbon monoxide, 0.66 weight percent of carbon dioxide, 40.60 weight percent of hydrogen; 40.85 weight percent of nitrogen, 0.57 weight percent of argon, and no oxygen.

The temperature profiles illustrated in FIGS. 2 and 3 represent typical profiles. However, as indicated hereinabove, depending on the conditions of operation, the temperature profile could indicate a plurality of maxima temperatures in the middle zone rather than a single maximum temperature in the middle zone.

The gaseous mixture resulting from the synthesis gas formation reaction comprises carbon monoxide, hydrogen, and nitrogen. Under the conditions employed in the synthesis gas generation reactor in the method of this invention, nitrogen does not react to form nitrogen oxides which would have a deleterious effect on the subsequent conversion of the synthesis gas in the presence of a Fischer-Tropsch catalyst. Hydrogen and carbon monoxide are present in the product mixture at a molar ratio of hydrogen to carbon monoxide in the range of from about 1.3 to about 2.2, preferably from about 1.9 to about 2.1. This product stream is particularly suitable for direct use, and without further purification, in the subsequent Fischer-Tropsch conversion of the synthesis gas to higher molecular weight hydrocarbons. When water or steam is present in the feed to the synthesis gas generation step, some reforming of the feedstock alkane would also occur; and, in that case, hydrogen and carbon monoxide are present in the product mixture at a molar ratio of hydrogen to carbon monoxide of at least 1.3 and up to at least 4. Thus, water could be employed as a component of the reaction mixture in order to adjust the molar ratio of the hydrogen to carbon monoxide produced, if necessary or desired.

The product mixture from the synthesis gas generation step is then contacted with a Fischer-Tropsch catalyst in a reactor to form primarily aliphatic hydrocarbons by the following unbalanced synthesis gas reaction:

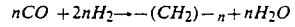
$$nCO + 2nH_2 \rightarrow -(CH_2)-_n + nH_2O$$

where n is in the range of 1 to 40, as illustrated by specific examples hereinbelow.

Suitable Fischer-Tropsch catalysts for use in the synthesis gas conversion of the preferred method of the present invention include any Fischer-Tropsch catalyst which is reported in the literature and which is capable of converting synthesis gas to hydrocarbons at a pressure in the range of from about zero to about 50 pounds per square inch gauge. Among such catalysts are those reported in H. H. Storch, N. Golumbic, and R. B. Anderson, *The Fischer-Tropsch and Related Syntheses*, John Wiley & Sons, Inc., New York, New York (1951). Typically a suitable Fischer-Tropsch catalyst comprises a primary catalytic component such as a cobalt component or another Group VIII metal component such as an iron, nickel or ruthenium component or a combination of such other Group VIII metal component and a cobalt component. A suitable Fischer-Tropsch catalyst can also contain a moderating or promoting component such as a magnesium component, a thorium component or a magnesium-thorium component.

Furthermore, although the aforesaid primary catalytic component and, if used, moderating or promoting component can be employed in the absence of a support component therefor or of an inert diluent, the primary catalytic component and, if used, moderating or promoting component can be supported on a suitable support material or can be employed in homogeneous admixture with an inert diluent. Materials that are suitable for use as such support or diluent comprise refractory particles. Suitable refractory materials that are inert under the conditions employed include the following: coarse sand, pebbles, stone, crushed rock; metal powders and metallic alloy powders (for example, aluminum, copper, silver, cobalt, carbon steel, stainless steel, brass, bronze, and Dural); powders of certain forms of carbon (for example, cokes, graphites, carbon blacks, and petroleum cokes); carbides of certain elements that are inert under the reaction conditions including higher carbides and complex ternary or quaternary carbides (for example, silicone carbide, boron carbide, carbides of metals from Group IVB, VB, VIB, or VIIB such as tungsten carbide, titanium carbide, tantalum carbide, niobium carbide, molybdenum carbide, thorium carbide, and manganese carbide); mixed metal carbide phases with nitrogen, boron, silicon (for example, iron carbonitride, and molybdenum-tungsten carbonitride); silicone powder; powders of metal silicides or silicone alloys (for example, ferrosilicone, magnesium silicide, magnesium ferrosilicide, manganese silicide, and silicone-aluminum alloy); metallic and nonmetallic nitrides (for example, tantalum nitride, tungsten nitride, mixed zirconium-vanadium nitride, boron nitride, silicone nitride, and aluminum nitride; and metal borides (for example, aluminum boride, thorium boride, and manganese boride). In the alternative and preferably, the refractory material comprises a porous, amorphous refractory inorganic oxide comprising an oxide of an element from Group IIA, IIIA, IIIB, IVA, or IVB of the Periodic Table. More preferably, the amorphous refractory inorganic oxide employed in the synthesis gas conversion step of the method of this invention comprises diatomaceous earth, zirconia, silica, alumina, silica-alumina, silica-stabilized alumina, phosphated alumina, silica-stabilized phosphated alumina, alumina-aluminum phosphate, boria-alumina, magnesia-alumina, boria, magnesia, titania, or mixtures thereof. Most preferably, the catalyst comprises a cobalt component and a diatomaceous support or diluent.

If the aforesaid primary catalytic and/or moderating or promoting components are employed on a support and/or in admixture with separate particles of an inert diluent, the preferred concentrations of the aforesaid components on the supported catalyst or in the mixture generally depend on the particular catalytic and moderating or promoting components. For example, catalyst particles typically contain 0.1-60 weight percent of the primary catalytic component(s) (5-40 weight percent of a cobalt component in particular) and, if used, 0.1-5.0 weight percent of the moderating or promoting component(s), in each case calculated as the elemental metal of the component and based on the weight of the catalyst particles. A mixture of catalyst particles and inert diluent particles typically contains 15-30 weight percent of the primary catalytic component(s) and, if used, 0.2-3.0 weight percent of the moderating or promoting component(s), calculated as the elemental metal of the component and based on the weight of the bed of particles. The compositions of specific catalysts that are preferred for use in the synthesis gas conversion of the method of the present invention are as follows: 68 weight percent of diatomaceous earth, 18 weight percent of a cobalt-containing component, 1 weight percent of a magnesium-containing component, and 1 weight percent of a thorium-containing component, each such metal-containing component calculated as the elemental metal; 42 weight percent of diatomaceous earth, 28 weight percent of stannic oxide, 18 weight percent of a cobalt-containing component, and 2 weight percent of a magnesium-containing component, each such metal-containing component calculated as the elemental metal; 69 weight percent of diatomaceous earth, 17 weight percent of a cobalt-containing component, and about 1 weight percent of a magnesium-containing component, each such metal-containing component calculated as the elemental metal; and 52 weight percent of diatomaceous earth, 25 weight percent of a cobalt-containing component, and 1-2 weight percent of a magnesium-containing component, each such metal-containing component calculated as the elemental metal.

The Fischer-Tropsch catalysts containing a support either can be obtained commercially or can be prepared by any conventional techniques for incorporation thereof into or onto an aforesaid inert refractory material. For example, any convenient, conventional technique can be employed for this purpose, such as impregnation from solution, vapor deposition, intimate physical mixing, and the like. For example, soluble compounds of cobalt and magnesium, such as cobalt and magnesium nitrates, can be added to a sol or gel of an aforesaid amorphous refractory inorganic oxide. This composition is then thoroughly blended into the sol or gel mixture, and subsequently co-gelled by the addition of dilute ammonia solution. The resulting co-gelled material is then dried. In another method of preparation, the refractory inorganic oxide is gelled, dried, and cooled, and the resulting material is then impregnated with one or more solutions of a soluble compound of cobalt and magnesium. The support containing the metal compound or precursor thereof can then be calcined, thereby forming the oxides of cobalt and magnesium. The calcination conditions employed are preferably a temperature of from about 500° C. to about 1,050° C. for from about 2 hours to about 36 hours, and more preferably calcination in air at a temperature of from about 950° C. to about 1,050° C. for from about 4 hours to about 20 hours. The calcination step can be omitted; but, if so, the salt of the metal must be decomposed in the catalyst activation step which is described hereinbelow.

Preferably a soluble compound(s) of the aforesaid component(s)—for example, cobalt and magnesium nitrates—are precipitated with a basic solution—for example, sodium or potassium carbonate. Either the solution also contains a suspension of the support material, or the support material is mixed into the solution after the precipitation occurs. In either case, the resulting mixture is then filtered or centrifuged, and the resulting separated solids are washed with hot water and then, if desired, extruded, pelletized, or otherwise shaped. The resulting solids are then dried and, if desired, calcined as described hereinabove.

Prior to use in the synthesis gas conversion reaction of the method of this invention, it is highly desirable to activate the Fischer-Tropsch catalyst by treatment with a reducing agent such as hydrogen, at a temperature in the range of from about 320° C. to about 440° C.

This activation procedure is also effective in regenerating or rejuvenating a Fischer-Tropsch catalyst which, as a result of extensive use in the synthesis gas conversion step of the method of this invention, undergoes a loss of activity for the synthesis gas conversion reaction. For this purpose, shifted synthesis gas can also be employed to regenerate the catalyst. Shifted synthesis gas can be obtained by mixing water and synthesis gas (for example, the product stream from the synthesis gas generation step of the invention) and passing the resulting mixture over a commercial synthesis gas shifting catalyst—such as, a copper oxide-zinc oxide mixture—at about 300° C. and atmospheric pressure. In one example, use of a catalyst regenerated by treatment with shifted synthesis gas resulted in the conversion of 95 volume percent of the carbon monoxide in a stream comprising 20 volume percent of carbon monoxide, 40 volume percent of hydrogen and 40 volume percent of nitrogen to carbon dioxide, and the resulting stream comprised 16 volume percent of carbon dioxide, 50 volume percent of hydrogen, 33 volume percent of nitrogen and 1 volume percent of carbon monoxide. Shifted synthesis gas can also be produced by adding water to the feed to the synthesis gas generation step in the method of this invention.

One specific example of a suitable Fischer-Tropsch catalyst for use in the synthesis gas conversion of the present invention was prepared as follows: to an aqueous solution of 30.9 grams of $Co(NO_3)_2 \cdot 6H_2O$, 12 grams of $Mg(NO_3)_2 \cdot 6H_2O$ and 0.85 gram of $Th(NO_3)_4 \cdot 4H_2O$ in 1.5 liters of water at 70° C., a hot aqueous solution of 17.6 grams of anhydrous $Na_2CO_3$ was added with stirring to precipitate the cobalt, magnesium and thorium as their carbonates. The resulting precipitate was stirred for 10 minutes and then vacuum filtered through a Buechner funnel containing a cake of diatomaceous earth (Celite 512 from Manville Corp.). The resulting wet filter cake was washed with 1.5 liters of hot distilled water, and the resulting suspension was filtered again. This washing step was repeated twice. The final wet filter was then vacuum dried at 90° C.–95° C. The resulting catalyst contained 17.3 weight percent of cobalt, 1–2 weight percent of magnesium and 0.8 weight percent of thorium, calculated as the elemental metals and based on the weight of the catalyst.

For evaluation, the middle 3 inches of a stainless steel reactor having a 0.62-inch inside diameter and a 32-inch length was filled with 5 grams of the aforesaid Co-Mg-Th catalyst having a bulk density of 0.33 grams per cubic centimeter and a 18–40 mesh size. The reactor was heated to 400° C. and a stream of 25 liters of hydrogen was introduced into one end of the reactor and withdrawn through the second end of the reactor in a period of approximately 2 hours to activate the catalyst. Thereafter, the reactor was cooled to 150° C. and a feed stream of 17 volume percent of carbon monoxide, 34 volume percent of hydrogen and 49 volume percent of nitrogen was introduced into the reactor at a pressure of 1–2 pounds per square inch gauge, and the temperature of the reactor was gradually raised to 191° C. As a result of the heat generated in the exothermic conversion of the synthesis gas, the temperature of the catalyst bed rose to a level of from about 195° F.–197° F. The results of this operation after over 70 days of continuous operation are presented in Table 2.

A second example of a suitable Fischer-Tropsch catalyst for use in the synthesis gas conversion of the present invention was prepared introducing an aqueous solution of 5,190 grams of $Na_2CO_3$ in about 2 gallons of water into an aqueous solution of 9270 grams of $Co(NO_3)_2 \cdot 6H_2O$ and 3600 grams of $Mg(NO_3)_2 \cdot 6H_2O$ in 40 gallons of water at 75° C. with stirring. After stirring the solution for about 5 minutes, 3750 grams of diatomaceous earth (Filter-Cel from Manville Corp.) was added to the solution with stirring. After 15 minutes of stirring at 75° C., the resulting mixture was centrifuged. The centrifuge cake was washed with about 30 gallons of hot water and the resulting suspension was filtered again. This washing step was repeated twice. The final centrifuge cake was dried in air, and then mulled and extruded as 0.25-inch extrudates, which were dried in an oven at 105° C. The resulting catalyst contained 24 weight percent of cobalt and 1–2 weight percent of magnesium, calculated as the elemental metals and based on the weight of the catalyst.

For evaluation, a carbon steel reactor having a 0.75-inch inside diameter and a 32-inch length was packed in the upstream 4.5 inches thereof with 15 grams of diatomaceous earth pellets (Celite 408 from Manville Corp.) having a 0.16-inch diameter and a 5-inch length and 15 grams of the aforesaid catalyst having a bulk density of 0.6 grams per cubic centimeter and being a 0.25-inch diameter extrudate in the 4.5-inch middle portion of the reactor. The volume of the reactor downstream of the catalyst was empty. The reactor was heated to 400° C. and a stream of 50 liters of hydrogen was introduced into the upstream end of the reactor and withdrawn from the downstream end of the reactor in a period of approximately 2 hours to activate the catalyst. Thereafter, the reactor was cooled to 150° C., and a feed stream of 17 volume percent of carbon monoxide, 34 volume percent of hydrogen and 49 volume percent of nitrogen was introduced into the reactor at a pressure of 1.5 pounds per square inch gauge, and the temperature of the reactor was raised to 191° C. As a result of the heat generated in the exothermic conversion of the synthesis gas, the temperature of the catalyst bed rose to 195° C.–197° C. The results of this operation after 10 days of continuous operation are presented in Table 3.

A third specific example of a suitable Fischer-Tropsch catalyst for use in the synthesis gas conversion of the present invention was prepared as follows: to an aqueous solution of 30.9 grams of $Co(NO_3)_2 \cdot 6H_2O$ and 12.0 grams of $Mg(NO_3)_2 \cdot 6H_2O$ in about 2 liters of a suspension of 15 grams of diatomaceous earth (acid-washed Celite 219 from Manville Corp.) and of 10 grams of $SnO_2$ powder in water at 80° C., a hot aqueous solution of 17.3 grams of anhydrous $Na_2CO_3$ in 150 milliliters of water was added with stirring to precipitate the cobalt and magnesium as their carbonates. The resulting precipitate was stirred for 15 minutes and then vacuum filtered through a Buchner funnel. The resulting wet filter cake was washed with 1.5 liters of hot distilled water, and the resulting suspension was filtered again. This washing step was repeated twice. The final wet filter cake was then vacuum dried at about 95° C. The resulting catalyst contained 17.6 weight percent of cobalt, 1–2 weight percent of magnesium, and 22.2 weight percent of tin, calculated as the elemental metals and based on the weight of the catalyst.

For evaluation, the middle 8.75 inches of a stainless steel reactor having a 0.62-inch inside diameter and a 32-inch length was filled with a homogeneous 18-40 mesh mixture of 5 grams of the aforesaid catalyst having a bulk density of 0.36 gram per cubic centimeter and 16 grams of diatomaceous earth (Celite 408 from Manville Corp.). The reactor was heated to 400° C. and a stream of 25 liters of hydrogen was introduced into one end of the reactor and withdrawn through the second end of the reactor within a period of approximately 2 hours to activate the catalyst. Thereafter, the reactor was cooled to 150° C. and a feed stream of 20 volume percent of carbon monoxide, 40 volume percent of hydrogen and 40 volume percent of nitrogen was introduced into the reactor at a pressure of 1 pound per square inch gauge, and the temperature of the reactor was gradually raised to 199° C.-200° C. As a result of the heat generated in the exothermic conversion of the synthesis gas, the temperature of the catalyst bed rose to a level of about 203° C. The space velocity was 196 liters of feed stream per hour per liter of catalyst particles in the packed bed. The results of this operation after over 3 days of continuous operation are presented in Table 4.

Another specific example of a suitable Fischer-Tropsch catalyst for use in the synthesis gas conversion of the present invention was prepared as follows: to an aqueous solution of 30.9 grams of $Co(NO_3)_2 \cdot 6H_2O$, 12.0 grams of $Mg(NO_3)_2 \cdot 6H_2O$, 2.0 milliliters of a 50 weight percent solution of $Mn(NO_3)_4$ and 1.4 grams of $Zr(NO_3)_2 \cdot 5H_2O$ in 1.8 liters of a suspension of 25.0 grams of diatomaceous earth (Celite 512 from Manville Corp.) in water at 70° C., a hot aqueous solution of 17.3 grams of anhydrous $Na_2CO_3$ in 150 milliliters of water was added with stirring to precipitate the cobalt, magnesium, manganese and zirconium as their carbonates. The resulting precipitate was stirred for 10 minutes and then vacuum filtered through a Buchner funnel. The resulting wet filter cake was washed with 1.5 liters of hot distilled water, and the resulting suspension was filtered again. This washing step was repeated twice. The final wet filter was then vacuum dried at 90° C.-95° C. The resulting catalyst contained 16.5 weight percent of cobalt, 1-2 weight percent of magnesium, 1 weight percent of manganese, and 0.8 weight percent of zirconium, calculated as the elemental metals and based on the weight of the catalyst.

For evaluation, the middle 2.5 inches of a stainless steel reactor having a 0.62-inch inside diameter and a 32-inch length was filled with 5 grams of the aforesaid 18-40- mesh Co-Mg-Mn-Zr catalyst having a bulk density of 0.32 gram per cubic centimeter. The reactor was heated to 400° C. and a stream of 30 liters of hydrogen was introduced into one end of the reactor and withdrawn through the second end of the reactor within a period of approximately 2 hours to activate the catalyst. Thereafter, the reactor was cooled to 150° C., and a feed stream of 17 volume percent of carbon monoxide, 34 volume percent of hydrogen and 49 volume percent of nitrogen was introduced into the reactor at a pressure of 1-2 pounds per square inch gauge, and the temperature of the reactor was gradually raised to 204° C. As a result of the heat generated in the exothermic conversion of the synthesis gas, the temperature of the catalyst bed rose to a level of from about 210° C.-212° C. The results of this operation after over 17 days of continuous operation are presented in Table 5.

The synthesis gas conversion reaction of the method of this invention is highly exothermic; and, unless the reactors are cooled, the temperature of the contents of the synthesis gas conversion reactor would rise as a result of the heat generated by the conversion reaction. For example, the adiabatic temperature rise of the gas stream resulting from the heat generated by the aforesaid conversion of 50, 60 and 70 percent of the carbon monoxide in a stream of 17 volume percent of carbon monoxide, 33 volume percent of hydrogen and 50 volume percent of nitrogen is calculated to be 473° C., 568° C., and 663° C., respectively.

However, in order to afford desirable rates of the aforesaid synthesis gas conversion and desirable selectivities for the formation therefrom of products other than methane and carbon dioxide, the conversion temperature must be maintained in the range of from about 160° C. to about 240° C., preferably from about 180° C. to about 220° C. Therefore it is essential to remove a substantial portion of the exothermic heat generated therein in order to prevent the temperature from rising above the aforesaid range of from about 160° C. to about 240° C. One suitable method to effect this control of the temperature in the synthesis gas conversion reactor is to recycle a portion of the gas from the conversion reactor, preferably after removal therefrom of at least a portion of the desired products. However, in order to limit the adiabatic temperature rise to 32° C. or 21° C. for a 70 percent conversion of carbon monoxide in the aforesaid fresh feed stream containing 17 volume percent of carbon monoxide, the ratio of the flow rate of the recycled gas to the flow rate of the fresh feed gas must be 20 or 30, respectively.

Figure 4:
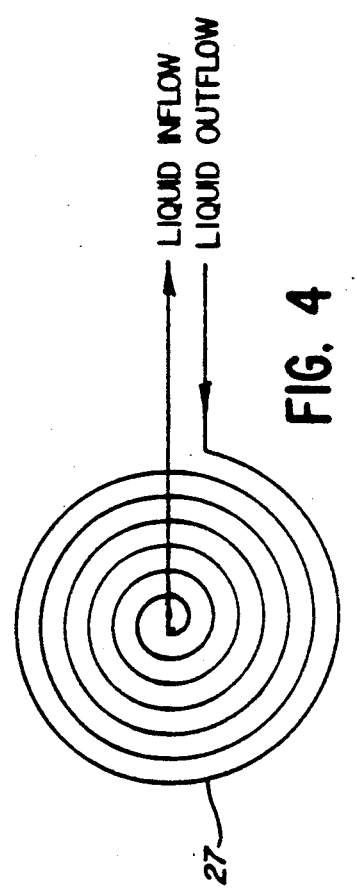
FIG. 4 is a top view of a preferred design of the cooling coils employed to control the temperature of the bed of particles employed in the reactor for the synthesis gas conversion reaction in the method of the present invention.

An alternative and preferred method for removing heat generated in the exothermic synthesis gas conversion and for controlling the temperature in the conversion reactor is the use of cooling means imbedded in the bed of Fischer-Tropsch catalyst particles. Although a variety of such cooling means are known, a particularly suitable means that combines both economy and efficiency is a plurality of pancake-shaped cooling coils imbedded in the bed of particles in the synthesis gas conversion reactor, such that the plane of the pancake-shaped coil is substantially perpendicular to the axis of the reactor and transverse to the direction of gas flow through the reactor. The particles in contact with and surrounding each such coil in the bed serve to diffuse the cooling effect of the coils throughout the entire catalyst bed. Helical coils 27 having a pancake shape have been found to be particularly suitable for this purpose, one preferred design thereof is illustrated in FIG. 4 but it is to be understood, however, that other coil or tube configurations or designs obvious to one skilled in the art guided by the disclosure herein, can be used and are sought to be covered hereby. The additional volume occupied by the catalyst bed, due to the presence therein of the number of coils that is necessary to effect the desired cooling, is less than 20 percent of the volume of the same bed but not containing such cooling coils.

The heat transfer coefficients of such coils were estimated using each of two such coils made from 0.50-inch or 0.25-inch outside diameter copper tubing. The 0.50-inch outside diameter tube was 18 feet in length and was coiled so as to form a 22-inch diameter coil with 7 turns and with a 1.5-inch center-to-center spacing between adjacent turns. The 0.25-inch outside diameter tubing was 38 feet in length and was coiled so as to form a 23-inch diameter coil with 15 turns and with a 0.75-inch center-to-center spacing between adjacent turns. In separate experiments, each series of tubes was imbedded in a bed of ceramic pellets measuring 0.19 inch by 0.25-inch such that the plane formed by the coils was substantially perpendicular to the axis of the reactor and transverse to the direction of gas flow through the reactor. For the coil made from the 0.50-inch outside diameter tubing, air at an initial temperature of about 45° C. was blown through the pellets at various velocities while water at an initial temperature of about 9° C. was passed through the coils at a rate of about 0.7 pound per second. For the coil made from the 0.25-inch outside diameter tubing, water at an initial temperature of about 9° C. was passed through the coil at a rate of about 0.2 pound per second while again air at an initial temperature of about 45° C. was blown through the pellets at various velocities. The average steady state temperature of the air exiting the bed at each air velocity was measured for each coil, and the air velocities and corresponding measured steady-state temperatures were employed to calculate overall heat transfer coefficients for each coil. The resulting heat transfer coefficients varied with the superficial velocity of air through the bed of pellets and, for each coil, are plotted against such superficial air velocities in FIG. 5.

Figure 5:
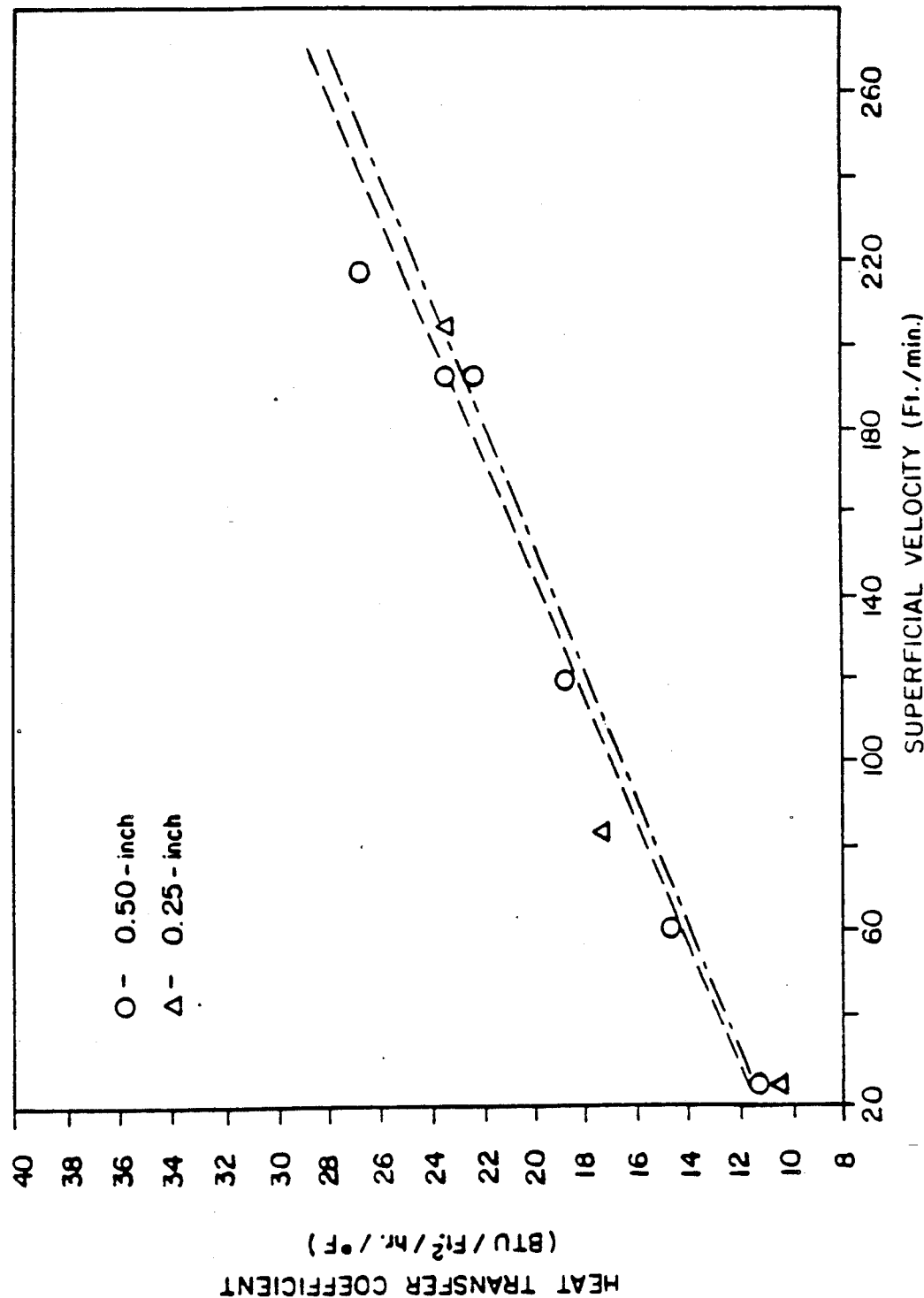
FIG. 5 contains plots of the heat transfer coefficients of each of two cooling coils differing in size and employed to control the temperature of the bed of particles employed in the reactor for the synthesis gas conversion reaction in the method of the present invention, versus the superficial velocities of the gas flowing through the particle bed and at which the heat transfer coefficients were measured.

The plots in FIG. 5 illustrate that, when the reaction mixture and resulting product mixture flow through a reactor at a superficial velocity of about 120 feet per minute, the heat transfer coefficient of such tubes and of the aforesaid other cooling tubes imbedded in the catalyst particles would be about 18-20 B.T.U. per square foot per degree Fahrenheit. Thus, the use of about 60 such coils or about 60 such series of tubes imbedded in the catalyst particles in a 30-foot long commercial-scale reactor, with each such coil spaced along the length of the conversion reactor about 6 inches from the adjacent coil, would provide the aforesaid necessary control of the temperature within the synthesis gas conversion reactor. Furthermore, the use of such cooling coils or tubes imbedded in the bed of particles in the synthesis gas conversion reactor does not result in a substantial pressure drop across the length of the bed.

It is to be understood that the above-described reactor apparatus, useful in regulating temperature in heterogeneous reaction systems, is one embodiment of the present invention and that the apparatus has many variations and applications.

A reactor apparatus useful in regulating temperature in a heterogeneous reaction systems in accordance with the present invention will be described with additional reference to FIGS. 6-9, and no unnecessary limitations are to be understood therefrom, as modifications within the scope of the invention will be obvious to those skilled in the art.

Referring to FIG. 6, a reactor apparatus, generally designated 50, useful in regulating temperature in a heterogeneous reaction system is shown. The reactor apparatus 50 includes an elongated tube reactor 52 packed with a bed of solid particles 54. The apparatus 50 includes a plurality of heat transfer medium tubes 56 or other passage means disposed or imbedded in the bed of solid particles 54. The heat transfer medium passage means may take a variety of different forms as will be later detailed herein. Generally, the heat transfer medium passage means comprises a plurality of tubes through which a heat transfer medium is passed. Such tubes may, if desired, be connected to each other in series, in parallel or in combination, e.g., some tubes or group(s) of tubes connected in series and some other tubes or group(s) of tubes connected in parallel. A reactant fluid phase is introduced through a feed line 60 into an entrance section 61 in the top portion 62 of the reactor 52. The fluid phase may be in a liquid or a gaseous form, such as the mixture of synthesis gas and nitrogen fed to the reactor 26 in FIG. 1.

Returning to FIG. 6, the reactant fluid phase of the heterogeneous reaction system is passed through the reactor 52 wherein the heat transfer medium tubes 56 are oriented such that they are substantially transversed to reactant flow through the reactor. (Note: associated heat transfer medium piping and connections are not shown as they may unnecessarily complicate the drawing.)

Further, adjacent tubes such as the tubes 56a, 56b and 56c (shown in FIG. 9 as coils similar to the coil 80 shown in FIG. 8, described below) are in spaced relationship relative to each other about the longitudinal axis (A) of the reactor 52.

The reactant fluid phase accumulates in a bottom exit section 63 as it is passed from the reactor 50 by means of an exit line 64.

The heat transfer medium passage means may be in a variety of different forms and made with various materials of construction. For example, the passage means will generally comprise tubing or piping configured in a variety of shapes such as a helical pancake shaped coil, as shown in FIG. 4, a serpentine tube 70 as shown in FIG. 7 or a sandwiched spiral coil 80, as shown in FIG. 8.

Further, with respect to FIG. 7, the serpentine tube form passage means 70 comprises two mirror image serpentine shape tubes 71 and 72 having a common central inlet header 73 and each having a peripheral outlet 74 and 75, respectively, with each tube having 5 turns or bends 76. It is of course to be understood that FIG. 7 illustrates just one embodiment of a serpentine tube form passage means and that other serpentine tube form passage means such as those including one or a plurality of tubes, separate headers, peripheral inlet(s), central outlets(s), greater or fewer numbers of bends, or various combinations of these features, for example, can be utilized without departing from the teachings herein.

Further, with respect to FIG. 8, the coil 80 comprises two spiral coil portions 82 and 84 interposed in the same tube axial plane XV. An S-shaped connector 86 connects the two spiral coil portions 82 and 84 to permit the continuous flow of the heat transfer medium therethrough.

Generally, because of heat transfer considerations, tubing or piping of a generally circular cross section will be preferred for use in the practice of the present invention but the invention is to be understood to be not so limited. For example, tubing or piping of a rectangular, square, oblong, etc., cross section may, if desired, be used without departing from the spirit of the invention.

Further, tubing or piping used for heat transfer medium passage means will, because of heat transfer considerations, generally be of a metallic material, such as relatively low cost carbon steel, stainless steel, or copper or, depending on the corrosivity (reactants and/or products) and temperature to which the tubing or piping will be subjected, metals such as inconel or titanium, for example. It being understood that any metal known can be used in the practice of the invention provided it can effectively serve as a heat transfer medium passage means in the environment, including temperature and corrosivity, to which it will be exposed.

In general, at least some of the passage means will be disposed or imbedded in solid particles with a reactant fluid phase, e.g., gas or liquid, flowing through the reactor substantially perpendicular to the passage means. If desired, the reactor may be packed with a catalytic material, such as solid catalyst particles (with which reactions typically take place on the solid catalyst surface); inert, solid heat transfer media (with which reaction typically takes place in the fluid phase) or a mixture of catalyst and inert heat transfer media particles as described above. Fischer-Tropsch reactions and oxidative coupling reactions, such as disclosed in U.S. Pat. No. 4,751,336, and incorporated herein by reference, are examples of heterogeneous reaction systems wherein the reactor apparatus of the subject invention may be utilized in conjunction with a bed of solid particles comprising catalytic material. Synthesis gas generation and methane pyrolysis to acetylene are examples of heterogeneous reaction systems wherein the reactor apparatus of the present invention may be used with a bed of solid particles comprising inert heat transfer media so as to supplement the control or regulation of temperature therein. It is to be understood, however, that the reactor apparatus of the invention may be useful for regulating temperature in other heterogeneous reaction systems including other exothermic or endothermic reaction systems. Further, it is to be understood that, if desired, the bed of solid particles may comprise a mixture of catalytic material and inert heat transfer media, as described above.

Preferably, at least one set of adjacent heat transfer passage means (defined as 2 adjacent heat transfer passage means), and more preferably, substantially all adjacent heat transfer passage means are in staggered relationship relative to each other. This staggered relationship may be more readily discerned from the cross sectional partial view shown in FIG. 9. As shown in FIG. 9, the fluid flow passageway 91a formed by the coiled tube 56a is complimentary to the adjacent coiled tube 56b with the coiled tube 56b having a tube heat transfer surface 92b aligned with the fluid flow passageway 91a. In turn, the fluid flow passageway 91b formed by the coiled tube 56b is complimentary to the adjacent coiled tube 56c with the coiled tube 56c having a tube heat transfer surface 92c aligned with the fluid flow passageway 91b. While the fluid flow passageway 91c formed by the coiled tube 56c is complimentary to the adjacent coiled tube 56b with the coiled tube 56b having a tube heat transfer surface 92b aligned with the fluid flow passageway 91c formed by the tube 56c. In this fashion, the reactant fluid phase which passes through the fluid flow passageway 91a of the coiled tube 56a will come in closer proximity to the heat transfer surface area of the adjacent tube.

Generally, the solid particles contained in the bed 54 will be of a size of up to about one-half the surface-to-surface spacing between adjacent turns of a tube (e.g., FIG. 9 denotes the width between adjacent turns 56c' and 56c'' of coiled tube 56c by the length $L_2$) and, more preferably, up to about one-quarter the surface-to-surface spacing between adjacent turns of a tube.

In addition, if desired, the heat transfer tubes can be arranged in sections, such as with of 2 to 12 or more tubes per section, so that different heat transfer mediums or heat transfer medium(s) at different heat transfer medium conditions, such as different temperatures, may be circulated through each tube or section, if desired. Alternatively, or in addition, the passage means in a reactor may, if desired, be sectioned in such a fashion to result in sections of the reactor, with the sections having varying numbers of tubes therein. For example, assuming each section constitutes a constant longitudinal length of the reactor, passage means may be more closely spaced in a first of said sections as compared to a second of said sections, resulting in the first of said sections having a greater number of passage means as compared to the second of said sections. Of course, if desired, the reactor may be sectioned so that it contains sections constituting different longitudinal lengths of the reactor.

Thereby, the reactor of the present invention provides temperature control flexibility which is generally unavailable with conventional types of reactors.

Preferably, through these different techniques the average bed temperature in a majority, and more preferably, in substantially all, of the sections of the reactor can be maintained approximately constant.

Furthermore, with catalytic reaction systems, it is known that as a catalytic material ages, the most reactive zone in the reactor often moves from one location to another. Such movement is a major obstacle in effective control of temperature in conventional reactor designs. In the present reactor apparatus, however, the movement of the most reactive zones of the reactor, such as may result upon catalyst aging, can be compensated for more simply, such as by changing the temperature of the heat transfer medium passed to the heat transfer passage means in the various zones of the reactor.

In addition, the reactor apparatus of the present invention attains a higher heat transfer coefficient than is generally obtainable with conventional reactor types. As a result, less metal surface area, generally by factor of about 2 to 4, is required to regulate, e.g., remove, the heat of reaction. As a result, such reactor apparatuses generally have lower capital costs than conventional reactor apparatuses.

Accordingly, the temperature in a heterogeneous reaction system can be regulated or controlled by effecting flow of a heat transfer medium through the passage means, e.g., heat transfer medium tubes, in the above-described reactor apparatus. Specific heat transfer mediums and heat transfer medium conditions, including medium temperature and flow rate, can be selected by one skilled in the art and guided by the teachings herein to effect temperature regulation in the reaction system.

The presence of the inert diluent nitrogen in the stream passing through the synthesis gas conversion reactor in the method of this invention further assists in moderating the synthesis gas conversion reaction and avoiding the development of hot spots within the synthesis gas conversion reactor. In a typical Fischer-Tropsch operation performed in the absence of an inert diluent, as the synthesis gas is converted by this exothermic reaction, decreasing amounts of gas are available to carry away the heat of reaction. As a result of the high temperatures that result, hot spots develop in the catalyst bed, and undesirable products are formed. However, when the inert diluent nitrogen is present, the rate of synthesis gas conversion is reduced because the rate of diffusion of the synthesis gas to the reactive sites is lower and the hot products are swept out of the reactor in the stream of the inert diluent. The inert diluent also serves to reduce the partial pressure of the synthesis gas in the synthesis gas conversion reactor which results in the formation of less undesirable products such as alcohols and heavy waxes. In effect, the use of nitrogen as a diluent in the synthesis gas conversion step of the method of this invention aids in more evenly distributing over the length of the reactor the extent to which the conversion reaction takes place and thereby reduces the temperature increase in the reactor and the formation of hot spots in the catalyst bed as a result of the exothermic heat generated. The nitrogen also serves to assist in removing from the reactor whatever heavy waxes that are formed, in addition to reducing the amount of heavy waxes formed, and thereby reduces the frequency at which the catalyst must be regenerated in order to sustain synthesis gas conversion activity.

In this regard, the formation of such less desirable products is also reduced in the method of this invention by virtue of the fact that a synthesis gas conversion reaction is performed at a total pressure in the range of from about 1 to about 50 pounds per square inch gauge, preferably from about 1 to about 15 pounds per square inch gauge. In general, only sufficient pressure to overcome any back pressure in the conversion reactor and to move the reactant and product gas through such reactor is necessary. For example, with a gas passing at a superficial velocity of 120 feet per minute through a reactor measuring 30 feet in length and 20 feet in inside diameter and packed with a bed of particles which have a maximum dimension of 0.125-0.25 inch and in which are imbedded 60 pancake-shaped helical coils—each of which measures 1,286 feet in length and 1 inch in outside diameter and has about 40 turns, with a center-to-center spacing of 3 inches between adjacent turns—the pressure drops that develop between the inlet and outlet of the reactor are only 1.07-3.21 pounds per square inch depending on the size of the particles in the bed. Such pressure drops are sufficiently low to permit the synthesis gas conversion to be operated at the low pressure therefor employed in the method of this invention.

In a conventional Fischer-Tropsch reaction at a relatively high total pressure and without an inert diluent, as the synthesis gas conversion reaction proceeds, the volume of gas decreases and the gas velocity diminishes as the gas stream proceeds through the reactor. Thus, in a conventional Fischer-Tropsch reaction, most of the synthesis gas conversion is completed near the entrance of the reactor, and there is essentially no opportunity to control the reaction in order to more evenly distribute throughout the reactor the extent to which the reaction proceeds. By contrast, in the method of this invention, as a result of the use of nitrogen as an inert diluent and of the use of the relatively low total reaction pressures, it is possible and preferred to stage the conversion of the synthesis gas throughout the synthesis gas conversion reactor by effecting a gradient in the activity of the Fischer-Tropsch catalyst therein. For example, when it is desired to distribute the extent to which the synthesis gas conversion reaction proceeds over the full length of the synthesis gas conversion reactor and thereby to control both the conversion and the selectivity of the conversion reaction and to optimize the product yield therefrom, it is possible to increase the average activity of the Fischer-Tropsch catalyst in the bed of particles from the inlet to the outlet thereof. One suitable technique to accomplish this is to employ catalyst particles containing, for example, 10 weight percent of cobalt in the inlet zone of the synthesis gas conversion reactor where the concentration of synthesis gas in the total gas entering the reactor is, for example, about 20 volume percent, and to employ catalyst particles containing, for example, about 20 weight percent of cobalt in the middle zone of the synthesis gas conversion reactor where the concentration of the carbon monoxide in the total gas has decreased to only about, for example, 10-12 volume percent, and to employ catalyst particles containing, for example, about 30 weight percent of cobalt in the outlet zone of the synthesis gas conversion reactor where the concentration of carbon monoxide and the total gas stream passing through the reactor has decreased to about, for example, 5-8 volume percent.

Another and particularly advantageous procedure to effect the aforesaid activity gradient is by dilution of the Fischer-Tropsch catalyst particles with substantially inert particles, with the degree of dilution decreasing from the inlet to the outlet of the synthesis gas conversion reactor. Thus, for example, Fischer-Tropsch catalyst particles containing, for example, a 30 weight percent of cobalt can be employed throughout the length of the synthesis gas conversion reactor and can be diluted with decreasing amounts of inert particles from the inlet to the outlet of the reactor. In this way, only catalyst particles containing a single concentration of the active metal component need to be made, and the catalyst particles represent only a fraction of the volume of the synthesis gas conversion reactor.

Another preferred technique to effect the aforesaid activity gradient along the length of the synthesis gas conversion reactor is to maintain the temperature of the particles in the inlet portion thereof at a lower level in the range of from about 180° C. to about 200° C. and the temperature of the particles in the outlet portion thereof in the range of from about 200° C. to about 220° C., with the temperature of the particles generally increasing from the inlet portion to the outlet portion.

The synthesis gas conversion step is performed preferably at an average space velocity in the range of from about 80 to about 2,000 volumes of total gas per hour per volume of particles, more preferably in the range of from about 100 to about 500 volumes of total gas per hour per volume per particles in the synthesis gas conversion reactor, calculated at 0° C. and atmospheric pressure absolute.

The gaseous mixture resulting from the synthesis gas conversion step comprises the resulting hydrocarbon products, nitrogen and any remaining unreacted carbon monoxide and hydrogen. At least a portion of the desired hydrocarbon products are separated from the stream using any convenient, conventional method at a pressure in the range of from about 1 to about 50 pounds per square inch gauge, preferably from about 1 to about 15 pounds per square inch gauge. One suitable method to accomplish this separation involves first separating at least a portion of the liquefiable products—such as $C_7$-$C_{30+}$ hydrocarbons—which are higher boiling than the feedstock alkane by scrubbing the gaseous mixture in a suitable solvent such as oil or water at a sufficiently low temperature, that the aforesaid liquefiable products are selectively dissolved in it. The resulting liquefied products are recovered from the solvent, for example, by distillation of the oil or water. The remaining gaseous components of the product stream comprise remaining lower boiling products—such as $C_1$-$C_{15}$, nitrogen and any remaining unreacted carbon monoxide and hydrogen and pass through the solvent as a gaseous mixture. Typical compositions of the feed to such a scrubber operated at one atmosphere gauge and at either 40° C. or 50° C. and of the liquid and vapor streams withdrawn from the scrubber are illustrated in Table 6.

At least a portion of the lower boiling hydrocarbon products are next separated from at least a portion of this remaining gaseous mixture in a second separation step. One highly effective technique that combines both economy and efficiency involves passing the remaining gaseous mixture through a charcoal bed. The nitrogen and remaining unreacted carbon monoxide, hydrogen and the less desirable lower boiling hydrocarbon products pass through the charcoal bed faster than the desirable higher boiling hydrocarbon products. When the bed becomes saturated with the desirable higher boiling hydrocarbon products, such materials begin to emerge from the bed, and the bed is removed from service and replaced in service by a fresh charcoal bed. The adsorbed products are then removed from the saturated bed by desorption and collected. This separation step can be performed either by removing the bed from service as the lowest boiling product, for example, ethane, begins to emerge from the bed or, by removing the bed from service when higher boiling products, for example, butanes, begin to emerge from the bed.

The adsorption, or saturation step, is conducted at a lower temperature than the desorption or product-removal step. The gases enter the charcoal bed at a temperature, for example, below about 80° C. and at 1-50, preferably 1-15, pounds per square inch gauge. Under these conditions as much as 20-30 percent of the weight of the bed containing adsorbed products is made up by the adsorbed products. When the bed can hold no more hydrocarbon, as shown by the presence of higher hydrocarbons in the effluent gas from charcoal bed, the feed gas is stopped and superheated steam is passed into the bed. As the bed heats up, hydrocarbons are desorbed from it and pass out of the bed with excess steam and are condensed in a separate operation. When the bed has been heated to some temperature preferably in the range of 105° C. -350° C. and desorption of hydrocarbons has diminished substantially, the charcoal bed is cooled down and then returned to service. Any oleophilic charcoal works well, as do certain hydrophobic clays. In particular, coconut and bituminous charcoal have been shown to be both highly effective and inexpensive. A typical composition of the vent gas exiting from such a charcoal adsorber operated at 110° F. -150° F. and one pound per square inch gauge are illustrated in Table 7.

Although not necessary in the method of the present invention, additional control of the temperature in the synthesis gas conversion reactor is provided by recycling to the synthesis gas conversion reactor a portion of the product stream therefrom, preferably after removal therefrom of at least a portion of at least the heaviest hydrocarbon products in the aforesaid first separation, or after removal therefrom of at least a portion of the heaviest hydrocarbon products in the first separation step and at least a portion of the lighter hydrocarbon products in the second separation step. The recycled material further assists in the removal of the heat generated by the exothermic synthesis gas conversion reaction. Such recycle also permits any remaining unreacted synthesis gas to be converted in the synthesis gas conversion reactor. Thus, in the embodiment illustrated in FIG. 1, after removal of the higher boiler hydrocarbon products in the first separator 30, a portion of the remaining gaseous material is pumped (not shown) through the lines 31, 36, and 22 back to the synthesis gas conversion reactor 26 by operating the valve 37. In the alternative, and not shown in FIG. 1, a portion of the remaining gas mixture after the aforesaid second separation—that is, the gaseous effluent from the second separator 35 in FIG. 1—can be recycled back to the synthesis gas conversion reactor. In either case, the ratio of the flow rate of the product mixture stream from the first reactor to the second reactor-to-the flow rate of the portion of the gaseous product mixture recycled to the second reactor is in the range of from about 0.1 to about 30, preferably in the range of from about 0.3 to about 6.

The following examples illustrate the practice of the invention. It is to be understood that all changes and modifications which come within the spirit of the invention are desired to be protected and thus the invention is not to be construed as limited by these examples.

EXAMPLES

EXAMPLE 1

Actual operating data and parameters were obtained using a tubular syngas pilot plant reactor, schematically shown in FIG. 6 and described above. The reactor was 15 feet long and 17.25 inches in diameter and contained 60 cooling coils (with each coil having a shape configuration such as that shown in FIG. 8). These coils were uniformly vertically spaced one from another along the longitudinal axis of the reactor a distance of 3 inches coil center line to coil center line.

The cooling coils were grouped together in twelve zones (consecutively designated zones 1 through 12, with zone 12 at the top of the reactor and zone 1 at the bottom of the reactor), with each zone containing 5 of such cooling coils, with each coil being 11 feet long and being made of ¼ inch stainless steel tubing. A heat transfer medium of tempered, hot oil was passed ugh each of the coils. The reactor was loaded with 567 pounds of catalyst [cobalt/magnesium oxide/celite containing 21.1 weight percent cobalt (unreduced state) with a cobalt to magnesium ratio of 10 and also containing 6 weight percent of a binder material]. The experimental reactor was graded into twelve zones as shown in Table 8. 55 of the coils were imbedded in the graded catalyst material in the reactor. The remaining 5 coils were imbedded in an inert packing material at the top, feed end of the reactor (zone 12). This inert packing served as a flow distributor of the feed material.

A time period in which the pilot plant reactor was operating at or near steady state was chosen for analysis. During this period, the temperature in the reactor was steady, i.e., the temperature was neither rapidly increasing ("running away") nor was it rapidly decreasing ("dying"). The experimental operating conditions and results (bed temperature in the various reactor zones) for this period is shown in Table 9.

EXAMPLE 2

The pilot plant experience exemplified by the data in Table 9 of Example 1 was used to model a commercial reactor and reactor system capable of handling a heat load (at 80 percent conversion, 0.32 weight hourly space velocity and 55 percent syngas in the feed) on a commercial plant scale.

The design feed rate was 125MM SCFD of natural gas. A 89 percent CO yield from the syngas generator, giving a syngas feed of 17.1 percent CO and 34.4 percent H₂ was assumed. The amount of catalyst material was based on 0.32 lbs of natural gas per hour per pound of catalyst. The molecular weight of the syngas feed was taken as 18.96 lbs per mole. Thus, 4,231,115 lbs of catalyst was required. The catalyst grading scheme used in the pilot plant, as shown in Table 8, was assumed. With this grading scheme, the catalyst occupied 60 percent of the reactor volume and the remaining 40 percent of the reactor volume was filled with inert pellets. Based on a bulk density of 45.2 lbs of cubic foot, the required reactor volume was 156,275 cubic feet. The reactor diameter was taken as 15 feet. Thus, the reactor system capable of handling the specified heat load and design feed rate would require approximately 25 such reactors connected in parallel.

Both 1-inch and 2-inch diameter coils were examined for controlling temperature. Based on our previous experience with flow rates and diameters the linear velocity of gas at the inlet to each reactor would be 1.43 ft/sec. The results of the three different assumed design configurations, assuming a design conversion of 80 percent, are shown in Table 10.

The design configuration shown in Table 10 for configuration A produced a runaway reactor temperature after the first two coils.

As a result of the coils being spaced closer together in design B, the reactor of design B was calculated as capable of handling the designed heat load.

In design configuration C, 13 reactor pairs of two reactors in series utilizing 2-inch diameter coils were calculated as providing acceptable temperature regulation. With this configuration, a linear gas velocity through the reactors is twice that of a configuration having 25 reactors in parallel and containing 1-inch diameter coils (design configuration B). The higher velocity capability of design configuration C results in better heat transfer characteristics and less residence time in the adiabatic reaction zones.

EXAMPLE 3

Design configuration B of Example 2 was taken as a base case design and a number of calculations were made to determine the sensitivity of the design to various system parameter changes. In almost all cases, the perturbation examined would be controllable in the reactor by reasonable changes in the cooling fluid temperature, i.e., altering the cooling fluid temperature ±10° C. from the base case of 180° C.

In one study, a reactor design called for 120 coils (as described above), with a catalyst graded into four sections as shown in Table 11, wherein Section 1 generally corresponds to zones 8, 9, 10 and 11; Section 2 generally corresponds to zones 5, 6 and 7; Section 3 corresponds to zones 3 and 4; and Section 4 corresponds to zones 1 and 2, respectively. The catalyst bulk density would change stepwise in each section. The gas composition and properties would vary as the gas flowed through the reactor. The number of moles of gas would change as the reaction proceeded. The change of molar flow rate and gas composition would result in changing heat transfer parameters along the length of the reactor. The changing partial pressure of the reactants also would change the reaction rate at the selected axial locations. The one-dimensional model was used to estimate the gas composition of flow rate axially in the reactor. Table 12 shows the estimated parameters for this coil model reactor. In this case, the highest calculated heat duty was not at the first coil of the reactor but at coil 81.

This is because the catalyst bulk density changed from 21 to 29 at this point, while the CO and H₂ partial pressure changes did not yet significantly effect the reaction rate. However, the reaction could be brought under control by lowering the cooling fluid temperature in this zone from 180° C. to 170° C.

The effect of changing other system parameters could also be determined. For example, recycle will increase the flow rate and reduce the partial pressure reactants in the feed. Thus, recycle would mean that it would be possible to operate the reactors with more catalysts per unit volume, and less grading with the inerts. However, more catalysts will be required and the cost savings as a result of less inerts which is probably offset by the added cost of the recycle blower and additional catalyst requirements. Consequently, it is believed that with a 1 to 1 ratio of recycle to syngas feed to the converter, it is not necessary to grade the catalyst bed with inerts.

The controllability of the coiled reactor is very sensitive to the activity of the catalyst. Consequently, when very active catalysts are used it is likely that the catalysts will need to be diluted with an inert material to facilitate temperature control within the reactor.

From the above description, it is apparent that the objects of the present invention have been achieved. While only certain embodiments have been set forth, alternative embodiments and various modifications will be apparent from the above description to those skilled in the art. These and other alternatives are considered equivalents and within the spirit and scope of the present invention.

TABLE 1

| Catalytic Particles | Maximum Reactor Temperature (°C.) | Conversion of $CH_4$ (Mole %) | Yield of CO in Product (Mole %) | $H_2/CO$ Mole Ratio |
|---|---|---|---|---|
| No | 1060 | 65.5 | 41.5 | 1.7 |
| No | 830 | 45.0 | 28.8 | 1.5 |
| Yes | 1000 | 89.2 | 75.6 | 1.9 |
| Yes | 900 | 66.6 | 41.0 | 2.0 |
| Yes | 800 | 44.4 | 10.6 | 2.2 |

TABLE 2

| Days of Operation | Feed Gas Pressure[a] | Space Velocity[b] | % CO Conversion | Combined Selectivities | | |
|---|---|---|---|---|---|---|
| | | | | $C_1$[c] | $C_2$-$C_3$ | $C_4$+ |
| 72 | 3 | 99 | 70.5 | 10.6 | 8.4 | 81.0 |
| 73 | 3 | 99 | 70.7 | 10.7 | 8.4 | 80.9 |
| 74 | 3 | 99 | 69.6 | 10.3 | 8.5 | 81.2 |
| 75 | 3 | 142 | 56.2 | 9.6 | 9.2 | 81.2 |
| 76 | 0.5 | 143 | 51.9 | 11.0 | 9.8 | 79.2 |
| 77 | 10 | 139 | 67.4 | 8.2 | 7.4 | 84.4 |
| 78 | 10 | 142 | 65.5 | 8.2 | 7.7 | 84.1 |
| 79 | 10 | 205 | 51.6 | 8.3 | 8.0 | 83.7 |
| 80 | 10 | 205 | 50.4 | 8.5 | 8.1 | 83.4 |
| 82 | 0.5 | 210 | 36.5 | 11.8 | 10.4 | 77.8 |

[a]pounds per square inch gauge
[b]liters of feed per hour per liter of catalyst particles
[c]carbon dioxide and methane combined

TABLE 3

Carbon selectivity
(vol. %)

| | Hours on stream | | | | |
|---|---|---|---|---|---|
| | 238 | 241 | 253 | 265 | 277 |
| | Space velocity | | | | |
| | 316[a] | 316[a] | 316[a] | 316[a] | 316[a] |
| | (0.50)[b] | (0.50)[b] | (0.50)[b] | (0.50)[b] | (0.50)[b] |

TABLE 3-continued

Carbon selectivity (vol. %)

| | Vol. % CO conversion | | | | |
|---|---|---|---|---|---|
| | 50.5 | 50.6 | 50.1 | 49.5 | 49.5 |
| $CO_2$ | 2.8 | 2.8 | 2.7 | 2.6 | 2.7 |
| $C_1$ | 14.0 | 14.4 | 14.1 | 13.5 | 13.8 |
| $C_2$ | 3.2 | 3.3 | 3.2 | 3.1 | 3.2 |
| $C_3$ | 8.8 | 8.9 | 8.8 | 8.5 | 8.6 |
| $C_4$ | 10.1 | 10.2 | 10.1 | 9.8 | 9.9 |
| $C_5$ | 10.5 | 10.5 | 10.5 | 10.2 | 10.1 |
| $C_6$ | 9.3 | 9.3 | 9.4 | 9.1 | 8.9 |
| $C_7$ | 7.3 | 7.2 | 7.4 | 7.0 | 7.0 |
| $C_8$ | 5.7 | 5.5 | 5.6 | 5.5 | 5.5 |
| $C_9$ | 4.6 | 4.4 | 4.6 | 4.4 | 4.3 |
| $C_{10}$ | 3.4 | 3.2 | 3.4 | 3.3 | 3.2 |
| $C_{11}$ | 2.4 | 2.3 | 2.4 | 2.6 | 2.5 |
| $C_{12}$ | 2.1 | 1.9 | 2.0 | 2.0 | 2.0 |
| $C_{13}$ | 1.6 | 1.5 | 1.6 | 1.5 | 1.5 |
| $C_{14}$ | 1.4 | 1.2 | 1.3 | 1.1 | 1.1 |
| $C_{15}$ | 1.3 | 0.9 | 1.2 | 0.9 | 0.8 |
| $C_{16}$ | 1.0 | 0.7 | 1.0 | 0.7 | 0.6 |
| $C_{17}$ | 0.8 | 0.5 | 0.7 | 0.5 | 0.5 |
| $C_{18}+$ | 1.1 | 0.6 | 1.1 | 1.0 | 0.8 |
| Total | 91.4 | 89.3 | 91.1 | 87.3 | 87.0 |
| Unaccounted[c] | 8.6 | 10.7 | 8.9 | 12.7 | 13.0 |
| $C_4+$ Yield (vol. %) | 36.0 | 35.7 | 35.7 | 35.8 | 35.5 |

| | Hours on stream | | | | |
|---|---|---|---|---|---|
| | 289 | 301 | 313 | 325 | 337 |
| | Space velocity | | | | |
| | $316^a$ | $316^a$ | $316^a$ | $316^a$ | $280^a$ |
| | $(0.50)^b$ | $(0.50)^b$ | $(0.50)^b$ | $(0.50)^b$ | $(0.44)^b$ |
| | Vol. % CO conversion | | | | |
| | 49.7 | 46.9 | 48.3 | 47.8 | 50.4 |
| $CO_2$ | 2.7 | 2.5 | 2.6 | 2.6 | 2.7 |
| $C_1$ | 13.9 | 13.5 | 13.9 | 13.8 | 13.7 |
| $C_2$ | 3.2 | 3.1 | 3.2 | 3.2 | 3.3 |
| $C_3$ | 8.8 | 8.5 | 8.7 | 8.9 | 8.8 |
| $C_4$ | 10.1 | 10.0 | 10.0 | 10.0 | 10.2 |
| $C_5$ | 10.4 | 10.3 | 10.2 | 10.5 | 10.4 |
| $C_6$ | 9.1 | 9.1 | 9.0 | 9.3 | 9.2 |
| $C_7$ | 7.3 | 7.1 | 7.1 | 7.3 | 7.4 |
| $C_8$ | 5.6 | 5.6 | 5.2 | 5.5 | 5.5 |
| $C_9$ | 4.4 | 4.5 | 4.2 | 4.3 | 4.3 |
| $C_{10}$ | 3.3 | 3.3 | 3.1 | 3.3 | 3.3 |
| $C_{11}$ | 2.3 | 2.5 | 2.3 | 2.6 | 2.5 |
| $C_{12}$ | 1.9 | 1.9 | 1.5 | 1.7 | 2.0 |
| $C_{13}$ | 1.4 | 1.4 | 1.3 | 1.3 | 1.2 |
| $C_{14}$ | 1.0 | 0.9 | 0.8 | 0.8 | 0.9 |
| $C_{15}$ | 0.7 | 0.7 | 0.6 | 0.6 | 0.7 |
| $C_{16}$ | 0.6 | 0.5 | 0.4 | 0.5 | 0.6 |
| $C_{17}$ | 0.5 | 0.5 | 0.3 | 0.3 | 0.5 |
| $C_{18}+$ | 0.9 | 0.9 | 0.7 | 0.6 | 0.9 |
| Total | 88.1 | 86.8 | 85.1 | 87.3 | 88.1 |
| Unaccounted[c] | 11.9 | 13.2 | 14.7 | 12.7 | 11.9 |
| $C_4+$ Yield (vol. %) | 35.5 | 34.0 | 34.6 | 34.2 | 36.0 |

| | Hours on stream | | | | |
|---|---|---|---|---|---|
| | 349 | 361 | 373 | 385 | 397 |
| | Space velocity | | | | |
| | $280^a$ | $240^a$ | $240^a$ | $192^a$ | $192^a$ |
| | $(0.44)^b$ | $(0.37)^b$ | $(0.37)^b$ | $(0.30)^b$ | $(0.30)^b$ |
| | Vol. % CO conversion | | | | |
| | 51.6 | 56.7 | 54.8 | 67.1 | 66.1 |
| $CO_2$ | 2.8 | 3.2 | 3.0 | 4.2 | 3.9 |
| $C_1$ | 14.2 | 13.9 | 13.8 | 14.5 | 14.2 |
| $C_2$ | 3.4 | 3.3 | 3.3 | 3.5 | 3.4 |
| $C_3$ | 8.9 | 8.9 | 8.8 | 8.8 | 8.8 |
| $C_4$ | 10.1 | 10.3 | 10.1 | 10.2 | 10.2 |
| $C_5$ | 10.3 | 10.5 | 10.3 | 11.2 | 10.9 |
| $C_6$ | 9.2 | 9.3 | 9.1 | 9.3 | 9.1 |
| $C_7$ | 7.2 | 7.4 | 7.2 | 7.0 | 7.0 |
| $C_8$ | 5.3 | 5.5 | 5.3 | 5.2 | 5.8 |
| $C_9$ | 4.1 | 4.3 | 4.1 | 4.0 | 4.1 |
| $C_{10}$ | 3.2 | 3.3 | 3.3 | 3.0 | 3.1 |
| $C_{11}$ | 2.4 | 2.5 | 2.4 | 2.1 | 2.2 |
| $C_{12}$ | 1.8 | 1.9 | 1.8 | 1.7 | 1.7 |
| $C_{13}$ | 1.1 | 1.2 | 1.3 | 1.2 | 1.2 |
| $C_{14}$ | 0.8 | 0.9 | 1.0 | 1.0 | 0.9 |
| $C_{15}$ | 0.6 | 0.6 | 0.8 | 0.8 | 0.7 |
| $C_{16}$ | 0.4 | 0.5 | 0.6 | 0.6 | 0.6 |
| $C_{17}$ | 0.3 | 0.4 | 0.5 | 0.5 | 0.4 |
| $C_{18}+$ | 0.6 | 0.8 | 1.0 | 0.9 | 0.7 |
| Total | 86.7 | 88.7 | 87.7 | 89.7 | 88.9 |
| Unaccounted[c] | 13.1 | 11.3 | 12.3 | 10.3 | 11.1 |
| $C_4+$ Yield (vol. %) | 38.5 | 40.1 | 40.0 | 46.3 | 46.1 |

| | Hours on stream | | | | |
|---|---|---|---|---|---|
| | 409 | 421 | 456 | 469 | 498 |
| | Space velocity | | | | |
| | $140^a$ | $140^a$ | $140^a$ | $316^a$ | $316^a$ |
| | $(0.24)^b$ | $(0.24)^b$ | $(0.24)^b$ | $(0.50)^b$ | $(0.50)^b$ |
| | Vol. % CO conversion | | | | |
| | 77.8 | 78.4 | 80.0 | 44.2 | 45.0 |
| $CO_2$ | 6.0 | 6.1 | 6.7 | 2.4 | 2.4 |
| $C_1$ | 14.4 | 14.5 | 15.2 | 13.7 | 14.3 |
| $C_2$ | 3.5 | 3.6 | 3.8 | 3.4 | 3.5 |
| $C_3$ | 8.5 | 8.7 | 9.1 | 9.6 | 9.7 |
| $C_4$ | 10.0 | 10.3 | 9.9 | 10.8 | 10.9 |
| $C_5$ | 10.1 | 10.4 | 10.6 | 11.0 | 11.4 |
| $C_6$ | 7.4 | 9.0 | 9.6 | 9.4 | |
| $C_7$ | 6.9 | 7.3 | 3.9 | 7.7 | 7.5 |
| $C_8$ | 5.3 | 5.3 | 5.0 | 5.6 | 5.4 |
| $C_9$ | 4.1 | 4.3 | 3.9 | 4.4 | 4.0 |
| $C_{10}$ | 3.0 | 3.2 | 2.7 | 3.0 | 2.7 |
| $C_{11}$ | 2.3 | 2.4 | 1.7 | 2.2 | 1.8 |
| $C_{12}$ | 1.8 | 1.9 | 1.5 | 1.7 | 1.3 |
| $C_{13}$ | 1.3 | 1.4 | 0.9 | 1.3 | 1.0 |
| $C_{14}$ | 1.0 | 1.1 | 0.7 | 1.0 | 0.7 |
| $C_{15}$ | 0.7 | 0.8 | 0.5 | 0.8 | 0.5 |
| $C_{16}$ | 0.5 | 0.6 | 0.3 | 0.6 | 0.4 |
| $C_{17}$ | 0.4 | 0.5 | 0.2 | 0.4 | 0.3 |
| $C_{18}+$ | 0.6 | 0.9 | 0.2 | 0.6 | 0.2 |
| Total | 86.8 | 92.3 | 88.8 | 89.8 | 87.4 |
| Unaccounted[c] | 13.2 | 7.7 | 11.2 | 10.2 | 12.6 |
| $C_4+$ Yield (vol. %) | 52.6 | 52.6 | 52.2 | 31.5 | 31. |

[a] liters of feed per hour per liter of catalyst particles
[b] grams of carbon monoxide and hydrogen per hour per gram of cobalt (calculated as elemental cobalt) on the catalyst particles
[c] represents unrecovered waxes and analytical errors

TABLE 4

| Hours of Operation | % CO Conversion | % $CH_4$ Selectivity |
|---|---|---|
| 114.0 | 65.1 | 7.9 |
| 115.4 | 66.1 | 7.6 |
| 118.5 | 63.6 | 7.5 |
| 119.4 | 63.3 | 7.4 |
| 120.4 | 63.4 | 7.3 |
| 136.0 | 56.1 | 6.4 |
| 136.2 | 55.8 | 6.3 |

TABLE 5

| Hours of Operation | Space Velocity[a] | % CO Conversion | Selectivities | |
|---|---|---|---|---|
| | | | $C_1$ | $CO_2$ |
| 425.3 | 147 | 57.3 | 12.9 | 4.7 |
| 426.8 | 147 | 57.7 | 12.6 | 4.3 |
| 431.7 | 97 | 73.4 | 12.4 | 7.0 |
| 434.0 | 97 | 72.0 | 12.3 | 7.2 |
| 449.3 | 54 | 99.2 | 18.8 | 20.8 |
| 449.7 | 54 | 99.1 | 19.0 | 21.0 |
| 456.2 | 236 | 41.7 | 11.7 | 3.1 |
| 456.4 | 236 | 42.1 | 12.3 | 3.1 |
| 473.6 | 331 | 32.8 | 13.3 | 2.5 |
| 473.8 | 331 | 32.8 | 12.7 | 2.7 |
| 480.3 | 147 | 60.2 | 12.0 | 4.7 |
| 480.8 | 147 | 60.3 | 12.2 | 5.2 |
| 497.2 | 147 | 57.0 | 12.2 | 4.5 |
| 571.3 | 147 | 52.8 | 12.8 | 4.3 |

[a] liters of feed per hour per liter of catalyst particles

TABLE 6

| Feed Composition (Wt. %) | | 40° C. | | | 50° C. | | |
|---|---|---|---|---|---|---|---|
| | | Composition (Wt. %) of Withdrawn Streams | | Wt. % of Component in Gas | Composition (Wt. %) of Withdrawn Streams | | Wt. % of Component in Gas |
| | (Wt. %) | Liquid | Gas | | Liquid | Gas | |
| $C_1$ | 12.00 | 0.00 | 12.00 | 100 | 0.00 | 12.00 | 100 |
| $C_2$ | 7.06 | 0.00 | 7.06 | 100 | 0.00 | 7.06 | 100 |
| $C_3$ | 8.27 | 0.00 | 8.27 | 100 | 0.00 | 8.27 | 100 |
| $C_4$ | 8.61 | 0.01 | 8.60 | 100 | 0.01 | 8.60 | 100 |
| $C_5$ | 8.41 | 0.03 | 8.38 | 100 | 0.01 | 8.40 | 100 |
| $C_6$ | 7.87 | 0.07 | 7.80 | 99 | 0.04 | 7.83 | 99 |
| $C_7$ | 7.17 | 0.20 | 6.97 | 97 | 0.10 | 7.07 | 99 |
| $C_8$ | 6.41 | 0.49 | 5.92 | 92 | 0.24 | 6.17 | 96 |
| $C_9$ | 5.62 | 1.10 | 4.52 | 80 | 0.55 | 5.07 | 90 |
| $C_{10}$ | 4.88 | 2.03 | 2.85 | 58 | 1.14 | 3.74 | 77 |
| $C_{11}$ | 4.19 | 2.18 | 1.38 | 33 | 1.89 | 2.30 | 55 |
| $C_{12}$ | 3.57 | 3.00 | 0.57 | 16 | 2.39 | 1.18 | 33 |
| $C_{13}$ | 3.02 | 2.85 | 0.17 | 6 | 2.59 | 0.43 | 14 |
| $C_{14}$ | 2.54 | 2.49 | 0.05 | 2 | 2.41 | 0.13 | 5 |
| $C_{15}$ | 2.12 | 2.10 | 0.02 | 1 | 2.07 | 0.05 | 2 |
| $C_{16}$ | 1.77 | 1.77 | 0.00 | 0 | 1.76 | 0.01 | 1 |
| $C_{17}$ | 1.47 | 1.47 | 0.00 | 0 | 1.47 | 0.00 | 0 |
| $C_{18}$ | 1.21 | 1.21 | 0.00 | 0 | 1.21 | 0.00 | 0 |
| $C_{19}$ | 1.01 | 1.01 | 0.00 | 0 | 1.01 | 0.00 | 0 |
| $C_{20}$ | 0.30 | 0.30 | 0.00 | 0 | 0.30 | 0.00 | 0 |

TABLE 7

| Vent Gas Composition | Mole % |
|---|---|
| $N_2$ | 57-59 |
| CO | 7-9 |
| $CO_2$ | 1-1.5 |
| $C_1$ | 1.2-1.8 |
| $C_2$ | 0.2-0.3 |
| $C_3$ | 0.2-0.5 |
| $H_2$ | 6-10 |
| $H_2O$ | 22-23 |

TABLE 8

Reactor Loading

| Zone | Catalyst (lbs) | Celite 410 (lbs) | lbs catalyst ρBulk (ft³ reactor) |
|---|---|---|---|
| 12 | 0.0 | 67.9 | 0 |
| 11 | 40.5 | 36.5 | 20.59 |
| 10 | 40.5 | 36.5 | 20.59 |
| 9 | 40.75 | 36.75 | 20.72 |
| 8 | 40.5 | 36.5 | 20.59 |
| 7 | 40.1 | 30.9 | 20.39 |
| 6 | 40.1 | 30.9 | 20.39 |
| 5 | 40.1 | 30.9 | 20.39 |
| 4 | 58.0 | 27.5 | 29.49 |
| 3 | 58.0 | 27.5 | 29.49 |
| 2 | 84.0 | 0.0 | 42.71 |
| 1 | 84.0 | 0.0 | 42.71 |

Top entrance section: 70 lbs of ½-inch Denstone 99 alumina balls
Bottom exit section: 112.7 lbs of ½-inch Denstone 99 alumina balls
Total catalyst = 566.55 lbs
Cobalt loading on catalyst = 21.1% (unreduced)
Total cobalt = 119.54 lbs
Feed flow for 40% $N_2$ + 40% $H_2$ + 20% CO at WHSV of 0.32 lbs total feed/lbs catalyst-hr
 = 180.8 lbs total feed hr
 = 10.273 lb moles/hr, (CO + $H_2$ + $N_2$)
 = 65.0 scfm, (CO + $H_2$ + $N_2$)

TABLE 9

| Reactor Zone | Temperatures, °C. | | |
|---|---|---|---|
| | Oil In | Oil Out | Average Bed |
| 12 (no rxn.) | 209 | 212 | 238 |
| 11 | 204 | 205 | 217 |
| 10 | 200 | 200 | 214 |
| 9 | 203 | 203 | 215 |
| 8 | 194 | 196 | 213 |
| 7 | 194 | 195 | 214 |
| 6 | 198 | 198 | 214 |
| 5 | 202 | 202 | 216 |
| 4 | 193 | 193 | 215 |
| 3 | 199 | 200 | 216 |
| 2 | 185 | 186 | 213 |
| 1 (feed) (discharge) | 186 | 187 | 215 |

| Property | Feed Stream | Product Stream |
|---|---|---|
| Temperature, °C. | 215 | 215 |
| Pressure, psia | 28.7 | 28.2 |
| Flow, lb moles/hr | 10.29 | 9.11 |
| lbs/hr | 214.3 | 214.3 |
| ft³/min | 56.4 | 50.8 |
| Superficial velocity, ft/sec | 0.58 | 0.52 |
| Molecular weight lbs/lb mole | 20.83 | 23.53 |
| Density, lbs/ft³ | .0634 | .0704 |
| Viscosity, Cps | .0241 | .0232 |
| Heat Capacity, BTU/lb °F. | .351 | .335 |
| Thermal Conductivity BTU/hr ft °F. | .0394 | .0318 |

TABLE 10

| | Parameter | | |
|---|---|---|---|
| | A | B | C |
| Width between adjacent turns of the coiled tube, in. | 2 | 1 | 1.5 |
| OD of tube, in. | 1 | 1 | 2 |
| Longitudinal length of reactor between adjacent tubes, in. | 2.5 | 2.5 | 4 |
| Inlet gas temp., °C. | 210 | 210 | 210 |
| Gas density, lbs/ft³ | .0595 | .0595 | .0595 |
| Heat capacity, BTU/lb °C. | .679 | .679 | .679 |
| Velocity, ft/sec, all zones | 1.43 | 1.43 | 2.86 |
| Catalyst bulk density, lbs/ft³ | **20.59 | 20.59 | 20.59 |
| Heat of rxn., BTU/lb mole CO | $-.684 \times 10^5$ | $-.684 \times 10^5$ | $-.684 \times 10^5$ |
| KO, mol CO/lb cat hr | *$2.66 \times 10^7$ | $2.66 \times 10^7$ | $2.66 \times 10^7$ |
| EA, Cal/mol °C. | $2.15 \times 10^4$ | $2.15 \times 10^4$ | $2.15 \times 10^4$ |
| Wall temp., TW, °C. | 170 | 180 | 185 |
| Lambda, BTU/hr ft °C. | 1.13 | 1.13 | 1.8 |
| HW, BTU/hr ft² °C. | 53.76 | 53.76 | 80.64 |

*Note, this pre-exponential and combined partial pressure term is for fresh PQ catalyst and undiluted feed gas (17% CO, 34% $H_2$).
**Graded catalyst bed.
Where:
KO represents the reaction rate factor.
EA means reaction activation energy.
Lambda represents the effective bed thermal conductivity.
HW represents the bed to heat transfer surface heat transfer coefficient.

TABLE 11

CATALYST GRADING SCHEME

| Section | Vol. % Catalyst | Vol. % Inerts | Catalyst Bulk Density lbs Catalyst per cubic foot Reactor (Measured) |
|---|---|---|---|
| 1 | 46.9 | 53.1 | 20.6 |
| 2 | 50.9 | 49.1 | 20.4 |
| 3 | 63.8 | 36.2 | 29.5 |
| 4 | 100 | 0 | 42.7* |

TABLE 11-continued

CATALYST GRADING SCHEME

| Section | Vol. % Catalyst | Vol. % Inerts | Catalyst Bulk Density lbs Catalyst per cubic foot Reactor (Measured) |
|---|---|---|---|

The bulk density of pure catalyst measured in the laboratory is 45.2 lbs/ft$^3$.

TABLE 12

| Computer Run | Coil Number | Gas Density lbs./ft$^3$ | Gas Heat Capacity BTU lb °C. | Velocity* ft/sec | Catalyst Bulk Density lbs/ft$^3$ | Reaction Parameter $KO' = KO(F(P_{H2}, P_{co}))$ lb mole CO hr lb cat $KO' \times 10^{-7}$ | Lambda BTU/hr ft °C. | HW$_2$ BTU/hr ft °C. | TWall °C. |
|---|---|---|---|---|---|---|---|---|---|
| A | 1-2 | .0595 | .679 | 1.43 | 20.6 | 2.66 | 1.13 | 53.76 | 180 |
| B | 41-42 | .0652 | .666 | 1.29 | 20.4 | 2.54 | 1.13 | 46.86 | 180 |
| C | 81-82 | .0708 | .654 | 1.15 | 29.5 | 2.01 | 1.13 | 40.15 | 170-173 |
| D | 101-102 | .0736 | .648 | 1.09 | 42.7 | 1.27 | 1.13 | 36.79 | 172-175 |
| E | 119-120 | .0761 | .642 | 1.04 | 42.7 | 0.49 | 1.13 | 33.56 | 185-190 |

*(upward velocity) should be a constant. Rounding-off may result in some variations.

What is claimed is:

1. A reactor apparatus useful in regulating temperature in a heterogeneous reaction system, said apparatus comprising a reactor packed with a bed of solid particles through which a reactant fluid phase of said heterogeneous reaction system is passed, and having a plurality of heat transfer medium passage means disposed in said bed of solid particles with said passage means being substantially transverse to reactant flow through said reactor with adjacent passage means being in spaced relationship relative to each other about the longitudinal axis of said reactor.

2. The apparatus of claim 1 wherein said bed of solid particles comprises a catalytic material.

3. The apparatus of claim 2 wherein the heterogeneous reaction system comprises a synthesis gas conversion system wherein said fluid phase comprises synthesis gas and said catalyst comprises a Fischer-Tropsch catalyst.

4. The apparatus of claim 1 wherein at least one set of adjacent passage means are in staggered relationship relative to each other.

5. The apparatus of claim 4 wherein a first of said adjacent passage means forms a fluid flow passageway complimentary to a second of said adjacent passage means with the second of said adjacent passage means having a tube heat transfer surface aligned with said fluid flow passageway of the first of said adjacent passage means.

6. The apparatus of claim 1 wherein at least one of said passage means comprises a tube configured in a shape selected from the group consisting of a unidirectional spiral coil, a serpentine tube and a sandwiched spiral coil comprising two spiral coil portions interposed in the same tube axial plane with the two tube portions being connected with an S-shaped connector.

7. The apparatus of claim 1 wherein at least one of said passage means comprises a tube comprising a plurality of interconnected spaced tube segments with said solid particles being of a size up to about one-half the space between adjacent segments of said tube.

8. A reactor apparatus useful in regulating temperature in a heterogeneous reaction system during conversion of a gaseous feed comprising synthesis gas to C$_{2+}$ hydrocarbon, said apparatus comprising a reactor packed with a bed of particles comprising Fischer-Tropsch catalyst and having a plurality of tubes imbedded in said bed of particles, with said tubes having a heat transfer medium passing therethrough and being substantially transverse to feed flow through said reactor.

9. The reactor of claim 8 wherein at least one set of adjacent tubes are in staggered relationship relative to each other.

10. The apparatus of claim 9 wherein a first of said adjacent tubes forms a fluid flow passageway complimentary to a second of said adjacent tubes with said second of said adjacent tubes having a tube heat transfer surface aligned with said fluid flow passageway of said first of said adjacent tubes.

11. The apparatus of claim 8 wherein at least one of said tubes is configured in a shape selected from the group consisting of a unidirectional spiral coil, a serpentine tube and a sandwiched spiral coil comprising two spiral coil portions interposed in the same tube axial plane with the two tube portions being connected with an S-shaped connector.

12. The apparatus of claim 8 wherein at least one of said tubes comprises a plurality of interconnected spaced tube segments with said solid particles being of a size up to about one-half the space between adjacent segments of said tube.

13. The apparatus of claim 8 wherein said Fischer-Tropsch catalyst comprises a cobalt-containing component.

14. The apparatus of claim 13 wherein said cobalt-containing component is supported on a diatomaceous earth support.

15. The apparatus of claim 14 wherein said Fischer-Tropsch catalyst additionally comprises at least one of a magnesium-containing component, a thorium-containing component, a tin-containing component, a manganese-containing component or a zirconium-containing component.

16. A reactor apparatus useful in regulating temperature in a reaction system during conversion of a gaseous feed comprising carbon monoxide, hydrogen and nitrogen to C$_{2+}$ hydrocarbons, said apparatus comprising a reactor containing a bed of solid particles comprising Fischer-Tropsch catalyst maintained at a pressure in the range of from about 1 to about 50 pounds per square inch gauge, said apparatus having a plurality of pan-cake-shaped tubes disposed in said bed of particles and having a heat transfer medium passing therethrough to maintain the temperature in said reactor in the range of from about 160° C. to about 240° C., with said tubes being substantially transverse to feed flow with at least one of said tubes comprising a plurality of interconnected spaced tube segments with said solid particles being of a size up to about one-half the space between adjacent segments of said tube.

17. The apparatus of claim 16 wherein at least one set of adjacent tubes are in staggered relationship relative to each other.

18. The apparatus of claim 17 wherein a first of said adjacent tubes forms a fluid flow passageway complimentary to a second of said adjacent tubes with said second of said adjacent tubes having a tube heat transfer surface aligned with said fluid flow passageway of said first of said adjacent tubes.

19. The apparatus of claim 16 wherein at least one of said tubes is configured in a shape selected from the group consisting of a unidirectional spiral coil, a serpentine tube and a sandwiched spiral coil comprising two spiral portions interposed in the same tube axial plane with the two tube portions being connected with an S-shaped connector.

20. The apparatus of claim 16 wherein said solid particles are of a size up to about one quarter the space between adjacent segments of said tube.

21. The apparatus of claim 16 wherein said apparatus comprises a plurality of sections with a first of said sections comprising at least one of said tubes having a first heat transfer medium passing therethrough and a second of said sections comprising at least a second of said tubes having a second heat transfer medium passing therethrough.

22. The apparatus of claim 21 wherein said first and second heat transfer mediums are the same material but at different heat transfer medium conditions.

23. The apparatus of claim 21 wherein said first of said sections comprises a greater number of tubes than said second of said sections.

24. The apparatus of claim 21 with an average bed temperature in a majority of said sections being approximately constant.

25. The apparatus of claim 24 wherein said average bed temperature in substantially all of said sections is approximately constant.

26. A method of regulating temperature in a heterogeneous reaction system, said method comprising the step of:
effecting flow of a heat transfer medium through passage means in a reactor apparatus comprising:
a reactor packed with a bed of solid particles through which a reactant fluid phase of said heterogeneous reaction system is passed, said apparatus including a plurality of heat transfer medium tubes disposed in said bed of solid particles with said passage means being substantially transverse to reactant flow through said reactor with adjacent passage means being in spaced relationship relative to each other about the longitudinal axis of said reactor.

27. The method of claim 26 wherein at least one set of adjacent passage tubes are in staggered relationship relative to each other.

28. The method of claim 27 wherein a first of said adjacent tubes forms a fluid flow passageway complimentary to the second of said adjacent tubes with a second of said adjacent tubes having a heat transfer surface aligned with said fluid flow passageway of the first of said adjacent tubes.

29. The method of claim 26 wherein at least one of said heat transfer medium passage tubes is configured in a shape selected from the group consisting of a unidirectional spiral coil, a serpentine tube and a sandwiched spiral coil comprising two spiral coil portions interposed in the same tube axial plane with the two tube portions being connected with an S-shaped connector.

30. The method of claim 26 wherein at least one of said heat transfer medium passage tubes comprises a plurality of interconnected spaced tube segments with said solid particles being of a size of up to about one-half the space between adjacent segments of said tube.

31. The method of claim 30 wherein said solid particles are of a size up to about one-quarter the space between adjacent segments of said tube.

32. The method of claim 26 wherein said apparatus comprises a plurality of sections with a first of said sections comprising at least one of said tubes having a heat transfer medium passing therethrough and a second of said sections comprising at least a second of said tubes having a second heat transfer medium passing therethrough.

33. The method of claim 32 wherein said first and second heat transfer mediums are the same material but at different heat transfer medium conditions.

34. The method of claim 32 wherein said first of said sections of said apparatus comprises a greater number of tubes than said second of said sections.

35. The method of claim 32 wherein said apparatus has an average bed temperature in the majority of said sections being approximately constant.

36. The method of claim 35 wherein said average bed temperature of said apparatus in substantially all of said sections is approximately constant.

* * * * *

UNITED STATES PATENT OFFICE
CERTIFICATE OF CORRECTION

Patent No. 5,080,872      Dated  January 14, 1992

Inventor(s)  James L. Jezl, Robert F. Blanks, Michael A. Stasi

It is certified that error appears in the above-identified patent and that said Letters Patent is hereby corrected as shown below:

Column 28, line 38, delete "ugh" and substitute --through--
Column 30, line 62, delete "Carbon selectivity"
Column 30, line 63, delete "(vol.%)"
Column 31, line 2 delete "Carbon selectivity"
Column 31, line 3, delete "(vol.%)"
Column 31, above line 7 reading "2.8  2.8  2.7  2.6  2.7" insert
    --Carbon Selectivity (vol.%)--
Column 31, above line 32 reading "2.7  2.5  2.6  2.6  2.7" insert
    --Carbon Selectivity (vol.%)--
Column 31, above line 56 reading "2.8  3.2  3.0  4.2  3.9" insert
    --Carbon Selectivity (vol.%)--
Column 32, line 2, delete "Carbon selectivity"
Column 32, line 3, delete "(vol.%)"
Column 32, above line 17 reading "6.0  6.1  6.7  2.4  2.4" insert
    --Carbon Selectivity (vol.%)--
Column 32, line 22, delete "9.  .0" and substitute --9.0  9.0--
Column 32, line 23, delete "3.9 and substitute --6.9--
Column 32, line 35, delete "31." and substitute --31.5--

Signed and Sealed this

Twentieth Day of April, 1993

Attest:

MICHAEL K. KIRK

Attesting Officer      Acting Commissioner of Patents and Trademarks